US008455249B2

(12) United States Patent
Aburatani et al.

(10) Patent No.: US 8,455,249 B2
(45) Date of Patent: Jun. 4, 2013

(54) HIGHLY EFFECTIVE ANTI-CADHERIN ANTIBODY FOR INDUCTION OF ANTIBODY-DEPENDENT CELLULAR CYTOTOXICITY IN VIVO

(75) Inventors: Hiroyuki Aburatani, Tokyo (JP); Lilin Zhang, Tokyo (JP); Keisuke Ishii, Tokyo (JP); Katsushi Kouda, Tokyo (JP); Aya Sakamoto, Tokyo (JP); Keiko Katsumi, Tokyo (JP); Hiroshi Onishi, Tokyo (JP); Yoko Kayukawa, Tokyo (JP)

(73) Assignees: The University of Tokyo, Tokyo (JP); Perseus Proteomics Inc., Tokyo (JP)

( * ) Notice: Subject to any disclaimer, the term of this patent is extended or adjusted under 35 U.S.C. 154(b) by 0 days.

(21) Appl. No.: 13/318,422

(22) PCT Filed: Apr. 30, 2010

(86) PCT No.: PCT/JP2010/057694
§ 371 (c)(1),
(2), (4) Date: Feb. 7, 2012

(87) PCT Pub. No.: WO2010/126137
PCT Pub. Date: Apr. 11, 2010

(65) Prior Publication Data
US 2012/0136140 A1 May 31, 2012

(30) Foreign Application Priority Data

May 1, 2009 (JP) .................................. 2009-111834
Jan. 29, 2010 (JP) .................................. 2010-018416

(51) Int. Cl.
*C12N 5/07* (2010.01)
*C07K 16/00* (2006.01)
(52) U.S. Cl.
USPC ........................................ 435/344; 530/387.3
(58) Field of Classification Search
USPC ........................................................ 530/388
See application file for complete search history.

(56) References Cited

U.S. PATENT DOCUMENTS

| 4,618,577 | A | 10/1986 | Handley et al. |
| 5,286,647 | A | 2/1994 | Handley et al. |
| 5,994,524 | A | 11/1999 | Matsushima et al. |
| 6,024,956 | A | 2/2000 | Matsushima et al. |
| 6,048,972 | A | 4/2000 | Matsushima et al. |
| 6,051,229 | A | 4/2000 | Handley et al. |
| 6,051,387 | A | 4/2000 | Handley et al. |
| 6,051,693 | A | 4/2000 | Handley et al. |
| 6,068,840 | A | 5/2000 | Matsushima et al. |
| 6,090,924 | A | 7/2000 | Handley et al. |
| 6,245,894 | B1 | 6/2001 | Matsushima et al. |
| 7,214,775 | B2 | 5/2007 | Hanai et al. |
| 7,651,688 | B2 | 1/2010 | Hanai et al. |
| 7,655,228 | B2 | 2/2010 | Hanai et al. |
| 7,682,610 | B2 | 3/2010 | Hanai et al. |
| 7,682,611 | B2 | 3/2010 | Hanai et al. |
| 7,687,061 | B2 | 3/2010 | Hanai et al. |
| 7,708,992 | B2 | 5/2010 | Hanai et al. |
| 7,708,997 | B2 | 5/2010 | Hanai et al. |
| 7,718,175 | B2 | 5/2010 | Hanai et al. |
| 7,763,246 | B2 | 7/2010 | Hanai et al. |
| 2002/0082396 | A1 | 6/2002 | Matsushima et al. |
| 2003/0194406 | A1* | 10/2003 | Reinhard et al. ............ 424/155.1 |
| 2005/0272916 | A1 | 12/2005 | Hanai et al. |
| 2009/0169572 | A1* | 7/2009 | Nakatsuru et al. .......... 424/184.1 |
| 2010/0196371 | A1 | 8/2010 | Hanai et al. |
| 2011/0142838 | A1* | 6/2011 | Reiter et al. ................ 424/135.1 |

FOREIGN PATENT DOCUMENTS

| EP | 0 239 400 A2 | 9/1987 |
| JP | 1-59878 B2 | 12/1989 |
| JP | 2005-522982 A | 8/2005 |
| WO | WO 83/04313 A1 | 12/1983 |
| WO | WO 92/01047 A1 | 1/1992 |
| WO | WO 92/03918 A1 | 3/1992 |
| WO | WO 92/20791 A1 | 11/1992 |
| WO | WO 93/06213 A1 | 4/1993 |
| WO | WO 93/11236 A1 | 6/1993 |
| WO | WO 93/12227 A1 | 6/1993 |
| WO | WO 93/19172 A1 | 9/1993 |
| WO | WO 94/02602 A1 | 2/1994 |
| WO | WO 94/25585 A1 | 11/1994 |
| WO | WO 95/0143 A1 | 1/1995 |
| WO | WO 95/15388 A1 | 6/1995 |
| WO | WO 96/02576 A1 | 2/1996 |
| WO | WO 96/33735 A1 | 10/1996 |
| WO | WO 96/34096 A1 | 10/1996 |

(Continued)

OTHER PUBLICATIONS

Tsuiji et al., Cadherin Conformations Associated with Dimerization and Adhesion, Apr. 27, 2007, The Journal of Biological Chemistry, vol. 282, p. 12871-12882.*

May et al., Identification of a transiently exposed VE-cadherin epitope that allows for specific targeting of an antibody to the tumor neovasculature, Feb. 8, 2005, Blood, vol. 105, p. 4337-4344.*

Li et al. The Role of Intramolecular Epitope Spreading in the Pathogenesis of Endemic Pemphigus Foliaceus (Fogo Selvagem), May 27, 2003, the Journal of Experimental Medicine, vol. 197, p. 1501-1510.*

Harris et al. Assessing Genetic Heterogeneity in Production Cell Lines: Detection by Peptide Mapping of a Low Level Tyr to Gln Sequence Variant in a Recombinant Antibody, Nov. 1993, Biotechnology, vol. 11, p. 1293-1297.*

Ackermann et al. Influence of Cell- and Media-Derived Factors on the Integrity of a Human Monoclonal Anitbody After Secretion into Serum-Free Cell Culture Supernatants, Jan. 20, 1995, Biotechnology and Bioengineering, vol. 45, p. 97-106.*

(Continued)

*Primary Examiner* — Hong Sang
*Assistant Examiner* — Michael D Allen
(74) *Attorney, Agent, or Firm* — Birch, Stewart, Kolasch & Birch, LLP

(57) ABSTRACT

It is an object of the present invention to provide an anti-cadherin antibody having high antibody-dependent cellular cytotoxicity. The present invention provides an anti-cadherin antibody, which recognizes any one of an upstream region of EC1, a cadherin domain 4 (EC4) and a cadherin domain 5 (EC5), wherein an antibody-dependent cellular cytotoxicity at an antibody concentration of 1 μg/mL is 30% or more.

7 Claims, 14 Drawing Sheets

FOREIGN PATENT DOCUMENTS

| WO | WO 00/61739 A1 | 10/2000 |
| WO | WO 02/097395 A2 | 12/2002 |
| WO | WO 2007/102525 A1 | 9/2007 |
| WO | WO 2008/121160 A2 | 10/2008 |

OTHER PUBLICATIONS

Caron et al., Engineered humanized dimeric forms of IgG are more effective antibodies, 1992, Journal of Experimental Medicine, vol. 176, p. 1191-1195.*

International Search Report for International Patent Application No. PCT/JP2010/057694, mailed on Jul. 20, 2010.

Japanese-language Written Opinion for International Patent Application No. PCT/JP2010/057694, mailed on Jul. 20, 2010.

Shimoyama et al., "Molecular Cloning of a Human Ca2+-dependent Cell-Cell Adhesion Molecule Homologous to Mouse Placental Cadherin: Its Low Expression in Human Placental Tissues," The Journal of Cell Biology, vol. 109, Oct. 1989, pp. 1787-1794.

International Preliminary Report on Patentability and Written Opinion of the International Searching Authority, dated Nov. 10, 2011, for International Application No. PCT/JP2010/057694 and English translation (dated Dec. 22, 2011).

Klingelhöfer et al., "Amino-terminal domain of classic cadherins determines the specificity of the adhesive interactions", Journal of Cell Science, vol. 113, pp. 2829-2836, 2000 (Published online Jul. 20, 2000).

Nose et al., "Localization of Specificity Determining Sites in Cadherin Cell Adhesion Molecules", Cell, vol. 61, No. 1, pp. 147-155, Apr. 6, 1990.

Thompson et al., "Clustal W: improving the sensitivity of progressive multiple sequence alignment through sequence weighting, position-specific gap penalties and weight matrix choice", Nucleic Acids Research, vol. 22, No. 22, pp. 4673-4680, 1994.

Thompson et al., "The CLUSTAL_X windows interface: flexible strategies for multiple sequence alignment aided by quality analysis tools", Nucleic Acids Research, vol. 25, No. 24, pp. 4876-4882, 1997.

Yoshida et al., "Teratocarcinoma Cell Adhesion: Identification of a Cell-Surface Protein Involved in Calcium-Dependent Cell Aggregation", Cell, vol. 28, No. 2, pp. 217-224, Feb. 1982.

European Search Report issued in European Application No. 10769835.9 on Jan. 4, 2013, 6 pages.

* cited by examiner

Figure 1

| | | |
|---|---|---|
| E-cadherin_CDH1_ | DWVIPPISCPENEKGPFPKNLVQIKSNKDKEGKVFYSITGQGADTPPVGVFIIERETGWL | 60 |
| P-cadherin_CDH3_ | DWVVAPISVPENGKGPFPQRLNQLKSNKDRDTKIFYSITGPGADSPPEGVFAVEKETGWL | 60 |
| N-cadherin_CDH2_ | DWVIPPINLPENSRGPFPQELVRIRSDRDKNLSLRYSVTGPGADQPPTGIFIINPISGQL | 60 |
| E-cadherin_CDH1_ | KVTEPLDRERIATYTLFSHAVSSNGNAVEDPMEILITVTDQNDNKPEFTQEVFKGSVMEG | 120 |
| P-cadherin_CDH3_ | LLNKPLDREEIAKYELFGHAVSENGASVEDPMNISIIVTDQNDHKPKFTQDTFRGSVLEG | 120 |
| N-cadherin_CDH2_ | SVTKPLDREQIARFHLRAHAVDINGNQVENPIDIVINVIDMNDNRPEFLHQVVWNGTVPEG | 120 |
| E-cadherin_CDH1_ | ALPGTSVMEVTATDADDDVNTYNAAIAYTILSQDPELPDKNMFTINRNTGVISVVTTGLD | 180 |
| P-cadherin_CDH3_ | VLPGTSVMQVTATDEDDAIYTYNGVVAYSIHSQEPKDPHDLMFTIHRSTGTISVISSGLD | 180 |
| N-cadherin_CDH2_ | SKPGTYVMTVTAIDADD-PNALNGMLRYRIVSQAPSTPSPNMFTINNETGDIITVAAGLD | 179 |
| E-cadherin_CDH1_ | RESFPTYTLVVQAADLQGE---GLSTTATAVITVTDTNDNPPIFNPTTYKGQVPENEANV | 237 |
| P-cadherin_CDH3_ | REKVPEYTLTIQATDMDGD---GSTTTAVAVVEILDANDNAPMFDPQKYEAHVPENAVGH | 237 |
| N-cadherin_CDH2_ | REKVQQYTLIIQATDMEGNPTYGLSNTATAVITVTDVNDNPPEFTAMTFYGEVPENRVDI | 239 |
| E-cadherin_CDH1_ | VITTLKVTDADAPNTPAWEAVYTILN-DDGGQFVVTTNPVNNDGILKTAKGLDFEAKQQY | 296 |
| P-cadherin_CDH3_ | EVGRLTVTDLDAPNSPAWRATYLIMGGDDGDHFTITTHPESNQGILTTRKGLDFEAKNQH | 297 |
| N-cadherin_CDH2_ | IVANLTVTDKDQPHTPAWNAVYRISGGDPTGRFAIQTDPNSNDGLVTVVKPIDFETNRMF | 299 |
| E-cadherin_CDH1_ | ILHVAVTNVVPFEVSLTT---STATVTVDVLDVNEAPIFVPPEKRVEVSEDFGVGQEITS | 353 |
| P-cadherin_CDH3_ | TLYVEVTNEAPFVLKLPT---STATIVVHVEDVNEAPVFVPPSKVVEVQEGIPTGEPVCV | 354 |
| N-cadherin_CDH2_ | VLTVAAENQVPLAKGIQHPPQSTATVSVTVIDVNENPYFAPNPKIIRQEEGLHAGTMLTT | 359 |
| E-cadherin_CDH1_ | YTAQEPDTFMEQKITYRIWRDTANWLEINPDTGAISTRAELDREDFEHVKNSTYTALIIA | 413 |
| P-cadherin_CDH3_ | YTAEDPDK-ENQKISYRILRDPAGWLAMDPDSGQVTAVGTLDREDEQFVRNNIYEVMVLA | 413 |
| N-cadherin_CDH2_ | FTAQDPDRYMQQNIRYTKLSDPANWLKIDPVNGQITTIAVLDRES-PNVKNNIYNATFLA | 418 |
| E-cadherin_CDH1_ | TDNGSPVATGTGTLLLILSDVNDNAPIPEPRTIFFCER-NPKPQVINIIDADLPPNTSPF | 472 |
| P-cadherin_CDH3_ | MDNGSPPTTGTGTLLLTLIDVNDHGPVPEPRQITICNQ-SPVRQVLNITDKDLSPHTSPF | 472 |
| N-cadherin_CDH2_ | SDNGIPPMSGTGTLQIYLLDINDNAPQVLPQEAETCETPDPNSINITALDYDIDPNAGPF | 478 |
| E-cadherin_CDH1_ | TAELTHG-ASANWTIQYNDPTGESIILKPK-MALEVGDYKINLKLMDNQN--KDQVTTLE | 528 |
| P-cadherin_CDH3_ | QAQLTDD-SDIYWTAEVNE-EGDTVVLSLK-KFLKQDTYDVHLSLSDHGN--KEQLTVIR | 527 |
| N-cadherin_CDH2_ | AFDLPLSPVTIKRNWTITRLNGDFAQLNLKIKFLEAGIYEVPIIITDSGNPPKSNISILR | 538 |
| E-cadherin_CDH1_ | VSVCDCEGAAGVCRKAQPVEAGLQIPAILGILGGILALLILILLLLFLRRR---AVVKE | 585 |
| P-cadherin_CDH3_ | ATVCDCHGHVETC--PGPWKGGFILP----VLGAVLALLFLLLVLLLLVRKK---RKIKE | 578 |
| N-cadherin_CDH2_ | VKVCQCDSNGDCTDVDRIVGAGLGTGAIIAILLCIIILLILVLMFVVWMKRRDKERQAKQ | 598 |
| E-cadherin_CDH1_ | PLLPPEDDTRDNVYYYDEEGGGEEDQDFDLSQLHRG----LDARPEVT-RNDVAPTLMSV | 640 |
| P-cadherin_CDH3_ | PLLLPEDDTRDNVFYYGEEGGGEEDQDYDITQLHRG----LEARPEVVLRNDVAPTIIPT | 634 |
| N-cadherin_CDH2_ | LLIDPEDDVRDNILKYDEEGGGEEDQDYDLSQLQQPDTVEPDAIKPVGIRRMDERPIHAE | 658 |
| E-cadherin_CDH1_ | PRYLPRPANPD--EIGNFIDENLKAADTDPTAPPYDSLLVFDYEGSGSEAASLSSLNSSE | 698 |
| P-cadherin_CDH3_ | PMYRPRPANPD--EIGNFIIENLKAANTDPTAPPYDTLLVFDYEGSGSDAASLSSLTSSA | 692 |
| N-cadherin_CDH2_ | PQYPVRSAAPHPGDIGDFINEGLKAADNDPTAPPYDSLLVFDYEGSGSTAGSLSSLNSSS | 718 |
| E-cadherin_CDH1_ | SDKDQDYDYLNEWGNRFKKLADMYGGGEDD | 728 |
| P-cadherin_CDH3_ | SDQDQDYDYLNEWGSRFKKLADMYGGGEDD | 722 |
| N-cadherin_CDH2_ | SGGEQDYDYLNDWGPRFKKLADMYGGGDD- | 747 |

CHO                    CDH3 forced expression CHO

Figure 9
A
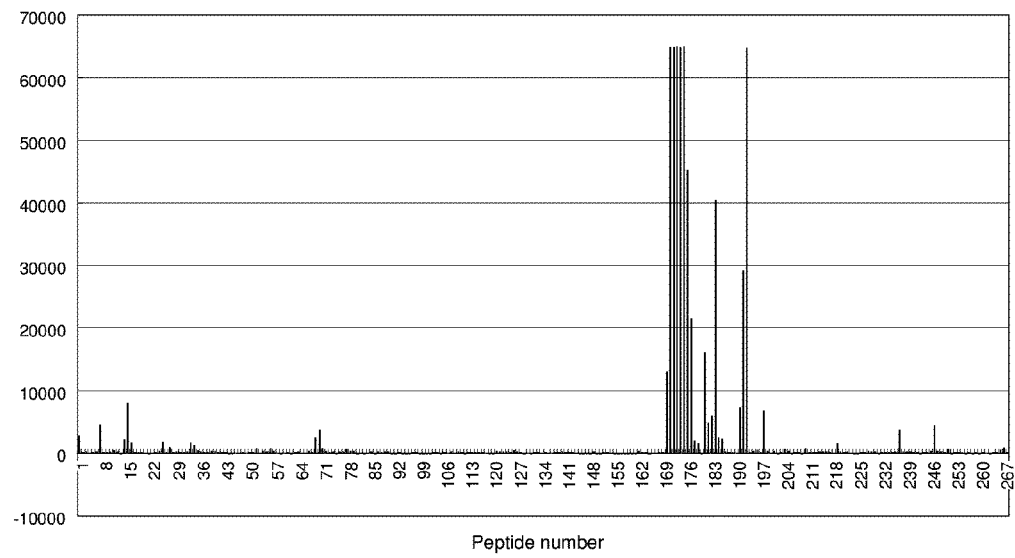
B
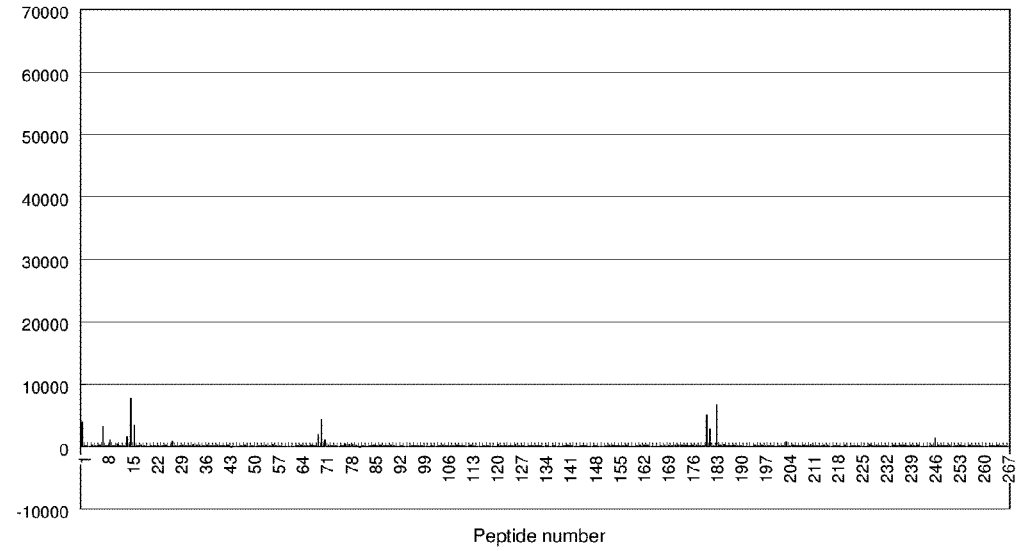

Figure 10
A
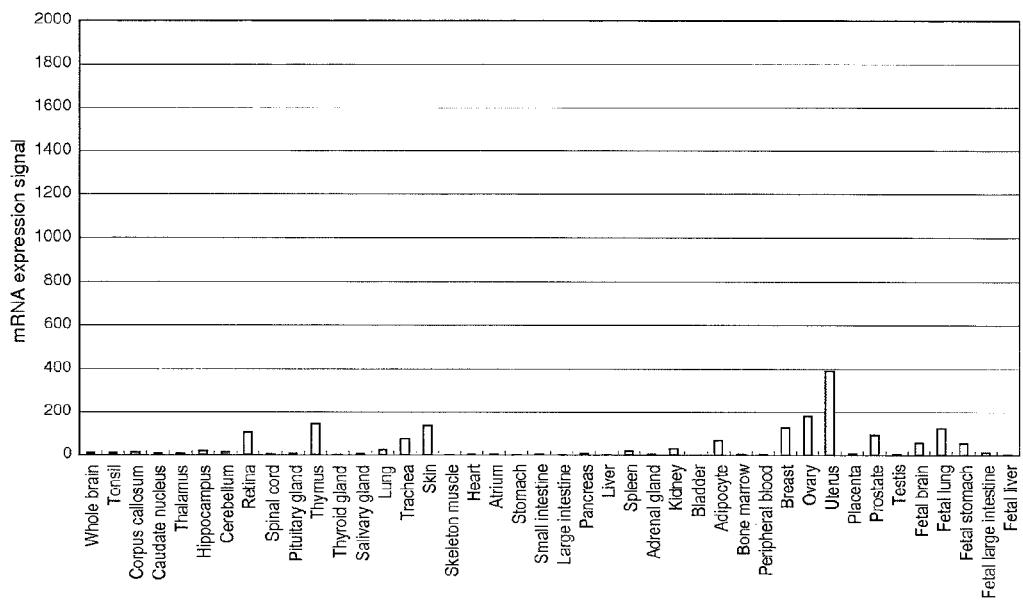
B
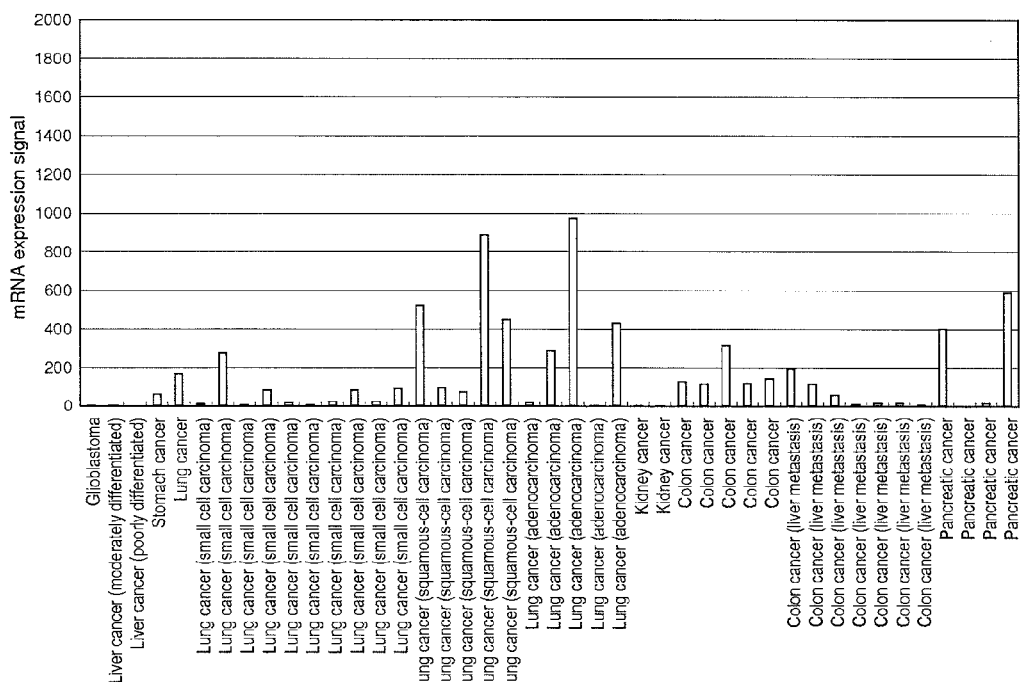

HIGHLY EFFECTIVE ANTI-CADHERIN ANTIBODY FOR INDUCTION OF ANTIBODY-DEPENDENT CELLULAR CYTOTOXICITY IN VIVO

TECHNICAL FIELD

The present invention relates to an anti-cadherin antibody that recognizes a specific domain of a cadherin and has high antibody-dependent cellular cytotoxicity.

BACKGROUND ART

Cancer is a crucial disease that becomes a leading cause of death, but the therapeutic needs thereof have not yet been satisfied. In recent years, in order to solve the problem of the conventional chemotherapy in that it affects even normal cells, a cancer treatment using a molecular-targeted agent has been vigorously studied. In this cancer treatment, an agent is designed to target a specific molecule that is specifically expressed in cancer cells, and the cancer is treated with the thus designed agent.

Cadherin is an example of molecules that can be a target of a molecular-therapeutic agent in a cancer treatment. Cadherin is a membrane protein that has been discovered as a molecule that is calcium-dependently associated with homophilic cell adhesion (Yoshida and Takeichi, Cell 28: 217-224, 1982). Proteins that have cadherin repeats (ECs) consisting of approximately 110 amino acid residues having high homology to one another are referred to as cadherin superfamily. There are 120 or more types of such proteins, and they play an important role in the maintenance of a multicellular organization.

An increase in the expression of a cadherin in cancer cells has been reported. With respect to cancer cells in which the expression level of a cadherin in cancer tissues is higher than that in normal tissues, the use of an agent prepared by binding an anticancer agent to an antibody recognizing a cadherin or an antibody having antibody-dependent cellular cytotoxicity (ADCC) for the therapy of cancers has been studied (WO2002/097395 and WO2007/102525).

Based on the characteristics of their structures, proteins belonging to the cadherin superfamily can be broadly classified into (1) classical cadherins, (2) desmosomal cadherins, (3) protocadherins, and (4) other cadherins. Classical cadherins that are main members of the cadherin superfamily are highly homologous to one another (FIG. 1). That is, the classical cadherin is a single transmembrane protein that seems to form a dimer, and it has five cadherin domains of EC1-EC5 in the extracellular region thereof and an intracellular domain. Cell adhesion via such a classical cadherin is characterized in that it is carried out between homologous cells. Cells mutually recognize the same species of cadherin molecules each having different expression status that is specific to cell species, so that cell adhesion is carried out. Homologous cells mutually adhere to each other based on a mechanism whereby an E-cadherin recognizes an E-cadherin and binds thereto and a P-cadherin recognizes a P-cadherin and binds thereto (FIG. 2).

Mutual recognition regarding a homologous/heterologous cadherin is considered to be caused by a cadherin domain 1 (EC1) located at the N-terminus of an extracellular domain (Nose A. et al., Cell 61: 147-155, 1990). Klingel et al. have reported that when the amino acid sequence at positions 1 to 213 of a human P-cadherin (SEQ ID NO: 2) is substituted with the corresponding region of a human E-cadherin, the resultant product does not bind to the E-cadherin but binds to the P-cadherin (Klingel H. et al., J of Cell Science 113: 2829-36, 2000). Hence, classical cadherins including an E-cadherin and a P-cadherin as typical examples are considered to mutually bind to one another by a single same mechanism.

In recent years, a large number of antibody drugs for use in cancer treatments have been actually placed on the market as molecular-targeted agents, and certain therapeutic effects can be obtained. Antibody-dependent cellular cytotoxicity (ADCC) is a main antitumor mechanism of commercially available anticancer agents such as trastuzumab and rituximab, and the increase of the ADCC activity leads to the improvement of therapeutic effects, reduction in side effects, etc. Thus, studies for searching for an antibody having higher ADCC activity and the development of a technique of enhancing ADCC activity have been carried out. For example, there have been developed a technique of removing fucose at the end of a sugar chain binding to the Fc portion of an antibody (WO00/61739) and a technique of substituting amino acids in the Fc portion with other amino acids to enhance affinity for effector cells, so as to increase ADCC activity (WO2008/121160).

As described above, a concept of using an antibody having ADCC activity as a therapeutic agent for cancer is publicly known. However, although there is a report regarding the association of a domain structure with the functions of classical cadherins including a P-cadherin, there are no reports suggesting the association of the level of ADCC activity with the structures of classical cadherins.

PRIOR ART DOCUMENTS

Patent Documents

[Patent Document 1] WO2002/097395
[Patent Document 2] WO2007/102525
[Patent Document 3] WO00/61739
[Patent Document 4] WO2008/121160

Non Patent Documents

[Non Patent Document 1] Yoshida and Takeichi, Cell 28: 217-224, 1982
[Non Patent Document 2] Nose A. et al., Cell 61: 147-155, 1990
[Non Patent Document 3] Klingel H. et al., J of Cell Science 113: 2829-36, 2000

SUMMARY OF INVENTION

Object to be Solved by the Invention

It is an object of the present invention to provide an anti-cadherin antibody having high antibody-dependent cellular cytotoxicity.

Means for Solving the Object

The present inventor has conducted intensive studies directed towards achieving the aforementioned object. The inventor measured the antibody-dependent cellular cytotoxic (ADCC) activity of P-cadherin antibodies, and as a result, the inventor found that the P-cadherin antibodies tend to be divided into two groups, depending on the level of the ADCC activity. Thus, the present inventor classified the antibodies based on a region recognized by each antibody. As a result, it was found that an antibody having high ADCC activity recognizes any one of an upstream region of EC1, a cadherin domain 4 (EC4) and a cadherin domain 5 (EC5) with high probability.

Elements that specify the ADCC activity of an antibody include: the affinity of the Fc region of an antibody for the Fc receptor of an effector cell; the affinity of an antibody for an antigen; and an epitope recognized by an antibody. For exertion of the ADCC activity, it is essential that an antibody bind to an antigen, and that the Fc receptor of an effector cell bind to the Fc region of the antibody. It is assumed that the binding of an effector cell to the Fc region of an antibody involves a spatial limitation due to a difference in a CDH3 region to which the antibody binds, and thus that a difference in the level of the ADCC activity would be made. The present invention has been completed based on these findings.

Specifically, the present invention provides the following.
(1) An anti-cadherin antibody, which recognizes any one of an upstream region of EC1, a cadherin domain 4 (EC4) and a cadherin domain 5 (EC5), wherein an antibody-dependent cellular cytotoxicity at an antibody concentration of 1 µg/mL is 30% or more.
(2) The antibody according to (1) above, wherein the cadherin is a P-cadherin.
(3) The antibody according to (1) or (2) above, which is an antibody produced by antibody-producing cells obtained from an immunized animal, into which a soluble P-cadherin has been administered as an immunogen.
(4) The antibody according to any one of (1) to (3) above, which is a monoclonal antibody.
(5) A hybridoma, which produces the antibody according to (4) above.
(6) A cytotoxic agent which comprises the antibody of any one of (1) to (4) above.
(7) The cytotoxic agent according to (6) above, which is administered to cancer cells.

In the present specification, the term "an upstream region of EC1" is used to mean a region consisting of 24 amino acid residues on the side upstream of the EC1 of each of an E-cadherin, a P-cadherin and an N-cadherin, and the corresponding regions of other cadherins.

Effect of the Invention

The anti-cadherin antibody of the present invention is characterized in that it recognizes any one of a upstream region of EC1, a cadherin domain 4 (EC4) and a cadherin domain 5 (EC5), and has high antibody-dependent cellular cytotoxicity. An antibody capable of exhibiting high antibody-dependent cellular cytotoxicity is useful as a material for producing a modified antibody or an engineered antibody. In addition, the anti-cadherin antibody of the present invention is administered to cancer in which a cadherin is expressed, so that the present antibody can exhibit anticancer action having antibody-dependent cytotoxicity as a mode of action. That is to say, the anti-cadherin antibody of the present invention is useful as an anticancer agent.

BRIEF DESCRIPTION OF DRAWINGS

FIG. 1 shows the sequences of mature proteins of an E-cadherin (CDH1), an N-cadherin (CDH2) and a P-cadherin (CDH3), wherein the signal and propeptide sequences are excluded.
FIG. 9 shows the results of the epitope analysis of PPMX13 using a peptide array. The numerical value on the X-axis indicates the number of the peptide array. A: PPMX13; and B: no primary antibodies.

EMBODIMENT FOR CARRYING OUT THE INVENTION

Figure 2:
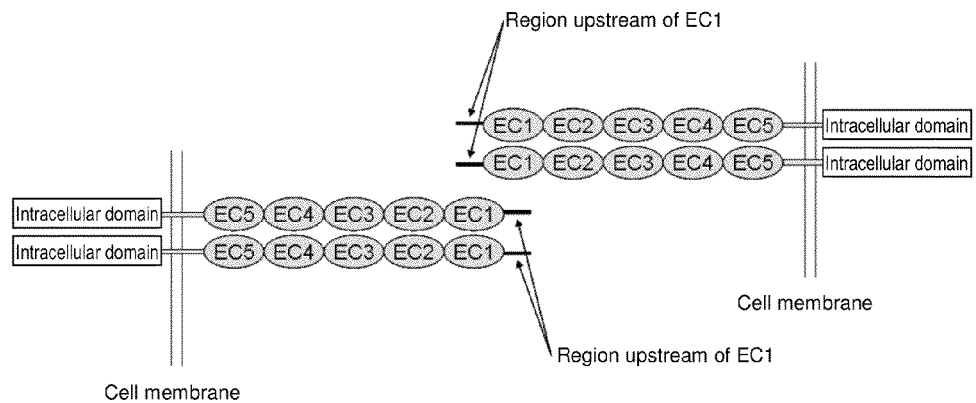
FIG. 2 shows the adhesion mechanism of molecules belonging to the classical cadherin family.

The present invention will be described more in detail below.

The antibody of the present invention is: an anti-cadherin antibody, which recognizes any one of an upstream region of EC1, a cadherin domain 4 (EC4) and a cadherin domain 5 (EC5), wherein an antibody-dependent cellular cytotoxicity at an antibody concentration of 1 µg/mL is 30% or more; an anti-cadherin antibody, which recognizes any one of an upstream region of EC1, a cadherin domain 4 (EC4) and a cadherin domain 5 (EC5), wherein an antibody-dependent cellular cytotoxicity at an antibody concentration of 0.1 µg/mL is 25% or more (which is, for example, stronger than the activity of PPMX5); or an anti-cadherin antibody, which recognizes any one of an upstream region of EC1, a cadherin domain 4 (EC4) and a cadherin domain 5 (EC5), wherein the maximum ADCC activity is 35% or more (which is, for example, stronger than the activity of PPMX6). Herein, the term "maximum ADCC activity" is used to mean ADCC activity obtained when an antibody concentration is increased and an increase in the ADCC activity reaches plateau.

In the present specification, the upstream region of EC1, the cadherin domain 1 (EC1), the cadherin domain 2 (EC2), the cadherin domain 3 (EC3), the cadherin domain 4 (EC4) and the cadherin domain 5 (EC5) of each of a P-cadherin, an E-cadherin and an N-cadherin are as described below. Moreover, the corresponding regions of other cadherins can be determined by making a comparison among the sequences of known cadherin proteins obtained from Genbank and the like. The sequences can be compared using a known program such as Clustal W2 (Thompson J D et al., Nucleic Acids Research 22 (22): 3673-3680, 1994) or Clustal X2 (Thompson J D et al., Nucleic Acids Research 25 (24): 4876-4882, 1997).

P-cadherin (CDH3)
Upstream region of EC1: amino acids at positions 108-131 of the amino acid sequence shown in SEQ ID NO: 2
Cadherin domain 1 (EC1): amino acids at positions 132-236 of the amino acid sequence shown in SEQ ID NO: 2
Cadherin domain 2 (EC2): amino acids at positions 237-348 of the amino acid sequence shown in SEQ ID NO: 2
Cadherin domain 3 (EC3): amino acids at positions 349-461 of the amino acid sequence shown in SEQ ID NO: 2
Cadherin domain 4 (EC4): amino acids at positions 462-550 of the amino acid sequence shown in SEQ ID NO: 2
Cadherin domain 5 (EC5): amino acids at positions 551-654 of the amino acid sequence shown in SEQ ID NO: 2

E-cadherin (CDH 1)
Upstream region of EC1: amino acids at positions 155-178 of the amino acid sequence shown in SEQ ID NO: 4
Cadherin domain 1 (EC1): amino acids at positions 179-283 of the amino acid sequence shown in SEQ ID NO: 4
Cadherin domain 2 (EC2): amino acids at positions 284-395 of the amino acid sequence shown in SEQ ID NO: 4
Cadherin domain 3 (EC3): amino acids at positions 396-507 of the amino acid sequence shown in SEQ ID NO: 4
Cadherin domain 4 (EC4): amino acids at positions 508-597 of the amino acid sequence shown in SEQ ID NO: 4
Cadherin domain 5 (EC5): amino acids at positions 598-704 of the amino acid sequence shown in SEQ ID NO: 4

N-cadherin (CDH2)
Upstream region of EC1: amino acids at positions 160-183 of the amino acid sequence shown in SEQ ID NO: 6
Cadherin domain 1 (EC1): amino acids at positions 184-288 of the amino acid sequence shown in SEQ ID NO: 6
Cadherin domain 2 (EC2): amino acids at positions 289-402 of the amino acid sequence shown in SEQ ID NO: 6
Cadherin domain 3 (EC3): amino acids at positions 403-518 of the amino acid sequence shown in SEQ ID NO: 6
Cadherin domain 4 (EC4): amino acids at positions 519-607 of the amino acid sequence shown in SEQ ID NO: 6
Cadherin domain 5 (EC5): amino acids at positions 608-719 of the amino acid sequence shown in SEQ ID NO: 6

The antibody-dependent cellular cytotoxicity (ADCC activity) can be measured by a known method. The numerical value of the ADCC activity of the present specification means antibody-dependent cellular cytotoxicity measured under the same measurement conditions as those in Example 4. Specifically, the ADCC activity can be measured as follows.

(1) Preparation of Effector Cells

Bone-marrow cells were collected from the femur of a C3H/HeJ Jcl mouse (8-week-old, male, CLEA Japan, Inc.), and the cells were then prepared to a concentration of $2\times10^6$ cells/mL in a 10% FBS-containing RPMI1640 medium. Thereafter, the cells were cultured for 6 days in the presence of 50 ng/mL human IL-2 (PEPROTECH) and 10 ng/mL mouse GM-CSF (PEPROTECH). On the day of measurement, the cells were recovered and were then washed with a 10% FBS-containing HAM medium, so as to prepare an effector cell solution.

(2) Preparation of Target Cells

As target cells, full-length CDH3-expressing CHO cells (EXZ1501) were used. The cells were removed from a plate, and were then suspended in a 10% FBS-containing HAM medium to a concentration of $1\times10^7$ cells/mL. Then, $^{51}$Cr was added to the suspension to a final concentration of 150 µCi. The thus obtained mixture was cultured in a 5% $CO_2$ incubator at 37° C. for 1.5 hours. The resultant cells were washed with a medium twice, and a 10% FBS-containing HAM medium was then added thereto. Thereafter, the cells were inoculated on a 96-well U-bottom plate (NUNC) to a concentration of $1\times10^4$ cells/mL, so as to prepare target cells.

(3) Measurement of ADCC Activity

An antibody solution, which had been prepared to have a concentration of each of 0.001, 0.01, 0.1 and 1 µg/mL, was dispensed in 50 µL/well into the target cells. The obtained mixture was incubated at room temperature for 15 minutes. Thereafter, 100 µL of the effector cells ($1\times10^5$ cells/well) was dispensed therein, and the obtained mixture was then cultured in a $CO_2$ incubator for 4 hours. Thereafter, a culture supernatant was recovered, and radioactivity in 100 µL of the culture supernatant was measured with a scintillation counter. Cytotoxicity can be obtained by the following formula.

$$\text{Cytotoxicity}(\%)=(A-C)/(B-C)\times100$$

A: the radioactivity value (cpm) of each antibody-added well
B: the radioactivity value (cpm) of a well, in which 100 µL of a 2% NP40 solution and 50 µL of a 10% FBS-containing RPMI medium have been added to the target cells
C: the radioactivity value (cpm) of a well, in which 150 µL of a 10% FBS-containing medium comprising the effector cells has been added to the target cells The type of a cadherin recognized by the antibody of the present invention is desirably a classical cadherin. Examples of the classical cadherin include, but are limited to, an E-cadherin, an N-cadherin, and P-cadherin.

As an antigen used to produce the antibody of the present invention, a cadherin or a partial peptide thereof can be used. An example of such an antigen that can be used herein is a soluble CDH3 protein. However, examples are not limited thereto.

The antibody of the present invention may be either a polyclonal antibody or a monoclonal antibody. The antibody of the present invention (a polyclonal antibody and a monoclonal antibody) can be produced by any one of various methods. Methods for producing such antibodies are well known in the present technical field [see, for example, Sambrook, J et al., Molecular Cloning, Cold Spring Harbor Laboratory Press (1989)].

(a) Preparation of Polyclonal Antibody

In order to produce a polyclonal antibody, a cadherin or a partial peptide thereof (which is preferably any one of an upstream region of EC1, a cadherin domain 4 (EC4) and a cadherin domain 5 (EC5)) is used as an antigen, and a mammal such as a rat, a mouse or a rabbit is immunized with this antigen. The applied dose of the antigen per animal is 0.1 to 100 mg, when no adjuvant is used It is 1 to 100 µg, when an adjuvant is used. Examples of the adjuvant include a Freund's complete adjuvant (FCA), a Freund's incomplete adjuvant (FIA), and an aluminum hydroxide adjuvant. Immunization is mainly carried out by injection into the vein, subcutis, abdominal cavity, etc. In addition, immunization interval is not particularly limited, and immunization is carried out at intervals of several days to several weeks, and preferably of 2 to 5 weeks, 1 to 10 times, and preferably 2 to 5 times. Then, six to sixty days after the final immunization, antibody titer is measured according to enzyme-linked immunosorbent assay (ELISA), enzyme immunoassay (EIA), radioimmunoassay (RIA), etc. Blood is collected on the day when the maximum antibody titer is obtained, and antiserum is then obtained.

When an antibody needs to be purified from the antiserum, it can be purified by selecting an appropriate method from known methods such as ammonium sulfate precipitation method, ion exchange chromatography, gel filtration, and affinity chromatography, or by combining such known methods.

(b) Preparation of Monoclonal Antibody

In order to produce a monoclonal antibody, first, a cadherin or a partial peptide thereof (which is preferably any one of an upstream region of EC1, a cadherin domain 4 (EC4) and a cadherin domain 5 (EC5)) is used as an antigen, and a mammal such as a rat, a mouse or a rabbit is immunized with this antigen. The applied dose of the antigen per animal is 0.1 to 100 mg, when no adjuvant is used. It is 1 to 100 μg, when an adjuvant is used. Examples of the adjuvant include a Freund's complete adjuvant (FCA), a Freund's incomplete adjuvant (HA), and an aluminum hydroxide adjuvant. Immunization is mainly carried out by injection into the vein, subcutis, abdominal cavity, etc. In addition, immunization interval is not particularly limited, and immunization is carried out at intervals of several days to several weeks, and preferably of 2 to 5 weeks, 1 to 10 times, and preferably 2 to 5 times. Then, one to sixty days, and preferably one to fourteen days after the final immunization, antibody-producing cells are collected. Examples of antibody-producing cells include splenic cells, lymph node cells, and peripheral blood cells. Of these, splenic cells and local lymph node cells are preferable.

To obtain cell fusion hybridomas, antibody-producing cells are fused with myeloma cells. As myeloma cells to be fused with antibody-producing cells, commonly available established cells from an animal such as a mouse can be used. Preferably, the used cell line has drug selectivity, cannot survive in a HAT selective medium (containing hypoxanthine, aminopterin and thymidine) when it is in an unfused state, and can survive only in a state in which it is fused with antibody-producing cells. Examples of myeloma cells include a mouse myeloma cell line such as P3X63-Ag.8.U1 (P3U1) and NS-1.

Subsequently, the aforementioned myeloma cells are fused with the aforementioned antibody-producing cells. For cell fusion, antibody-producing cells ($1 \times 10^6$ to $1 \times 10^7$ cells/ml) are mixed with myeloma cells ($2 \times 10^5$ to $2 \times 10^6$ cells/ml) in a medium used for culture of animal cells, such as DMEM or RPMI-1640 medium containing no serum (wherein the ratio between the antibody-producing cells and the myeloma cells is preferably 5:1), and fusion is then carried out in the presence of a cell fusion promoter. As a cell fusion promoter, polyethylene glycol having an average molecular weight of 1000 to 6000 Daltons, or the like can be used. Alternatively, the antibody-producing cells can also be fused with the myeloma cells using a commercially available cell fusion apparatus that utilizes electrical stimulation (for example, electroporation).

Hybridomas of interest are selected from the cells after completion of the cell fusion treatment. As a selection method, a cell suspension is appropriately diluted with a fetal bovine serum-containing RPMI-1640 medium, for example, and the thus diluted solution is then inoculated on a microtiter plate to a concentration of approximately $3 \times 10^5$ cells/well. Thereafter, a selective medium is added to each well, and the obtained mixture is then cultured, while appropriately exchanging the medium with a fresh selective medium. As a result, cells that grow approximately 14 days after initiation of the culture in the selective medium can be obtained as hybridomas.

Subsequently, whether or not an antibody of interest is present in a culture supernatant of the growing hybridomas is screened. The screening of the hybridomas may be carried out according to an ordinary method, and thus the screening method is not particularly limited. For example, an aliquot of the culture supernatant contained in the well in which the hybridomas have grown is collected, and thereafter, a hybridoma that produces an antibody binding to the upstream region of EC1, the EC4 domain or the EC5 domain of a cadherin can be screened. The cloning of the fused cells is carried out by a limiting dilution method or the like, and a hybridoma that is a monoclonal antibody-producing cell can be finally established.

As a method of collecting a monoclonal antibody from the thus established hybridomas, a common cell culture method, an ascites collection method or the like can be adopted. In the case of the cell culture method, hybridomas are cultured in an animal cell culture medium such as a 10% fetal bovine serum-containing RPMI-1640 medium, MEM medium or a serum-free medium under ordinary culture conditions (for example, at 37° C. in a 5% $CO_2$ concentration) for 7 to 14 days, and an antibody is then obtained from the culture supernatant.

In the case of the ascites collection method, hybridomas (approximately $1 \times 10^7$ cells) are administered into the abdominal cavity of an animal of the same species as a mammal, from which myeloma cells are derived, so that large quantities of hybridomas are allowed to grow. Then, one to two weeks later, the ascites is collected. When purification of an antibody is necessary in the above-described antibody collection method, the antibody can be purified by selecting an appropriate method from known methods such as ammonium sulfate precipitation method, ion exchange chromatography, gel filtration, and affinity chromatography, or by combining such known methods.

The type of the antibody of the present invention is not particularly limited. Any of a mouse antibody, a human antibody, a rat antibody, a rabbit antibody, a sheep antibody, a camel antibody, an avian antibody and the like, and a genetically recombinant antibody that is artificially modified for the purpose of reduction in heterogenetic antigenecity against human, such as a chimeric antibody and a humanized antibody, may be used. A genetically recombinant antibody can be produced by a previously known method. A chimeric antibody is an antibody consisting of the variable regions of heavy and light chains of a mammalian antibody other than a human antibody, such as a mouse antibody, and the constant regions of heavy and light chains of a human antibody. Such a chimeric antibody can be obtained by ligating DNA encoding the variable region of a mouse antibody to DNA encoding the constant region of a human antibody, then incorporating the thus ligated DNA into an expression vector, and then introducing the expression vector into a host, so as to produce an antibody of interest. A humanized antibody is prepared by transplanting the complementarity determining region (CDR) of a mammalian antibody other than a human antibody, for example, the CDR of a mouse antibody, into the CDR of a human antibody. A common genetic recombination method therefor has been known. Specifically, a DNA sequence designed such that the CDR of a mouse antibody is ligated to the framework region (FR) of a human antibody is synthesized by PCR method from several oligonucleotides produced such that they have some overlapping portions at the termini thereof. The obtained DNA is ligated to DNA encoding the constant region of a human antibody, and the thus ligated DNA is then incorporated into an expression vector. This expression vector is introduced into a host, so that the host generates a humanized antibody (EP239400, International Publication WO96/02576, etc.).

Also, a method of obtaining a human antibody has been known. For example, human lymphocytes are sensitized in vitro with a desired antigen or cells that express a desired antigen, and the thus sensitized lymphocytes are then fused with human myeloma cells such as U266, so as to obtain a desired human antibody having binding activity to an antigen (see JP Patent Publication (Kokoku) No. 1-59878 B (1989)). Alternatively, a transgenic animal having all repertories of human antibody genes is immunized with a desired antigen, so as to obtain a desired human antibody (see WO93/12227, WO92/03918, WO94/02602, WO94/25585, WO96/34096, and WO96/33735). Moreover, a technique of obtaining a human antibody by panning of a human antibody library has also been known. For example, the variable region of a human antibody is allowed to express as a single-stranded antibody (scFv) on the surface of a phage according to a phage display method, and a phage binding to an antigen can be selected. Then, by analyzing the gene of the selected phage, the sequence of DNA encoding the variable region of a human antibody binding to an antigen can be determined. If the DNA sequence of the scFv binding to the antigen is determined, a suitable expression vector is prepared from the sequence, and a human antibody can be then obtained. These methods have already been publicly known, and WO92/01047, WO92/20791, WO93/06213, WO93/11236, WO93/19172, WO95/01438 and WO95/15388 can be used as references.

These antibodies may be any of monovalent antibodies, divalent antibodies and polyvalent antibodies, unless they lose their characteristics in that they are: antibodies which recognize any one of an upstream region of EC1, a cadherin domain 4 (EC4) and a cadherin domain 5 (EC5), wherein an antibody-dependent cellular cytotoxicity at an antibody concentration of 1 μg/mL is 30% or more; antibodies which recognize any one of an upstream region of EC1, a cadherin domain 4 (EC4) and a cadherin domain 5 (EC5), wherein an antibody-dependent cellular cytotoxicity at an antibody concentration of 0.1 μg/mL is 25% or more (which is, for example, stronger than the activity of PPMX5); or antibodies which recognize any one of an upstream region of EC1, a cadherin domain 4 (EC4) and a cadherin domain 5 (EC5) wherein a maximum ADCC activity is 35% or more (which is, for example, stronger than the activity of PPMX6). Moreover, the antibodies may also be low molecular weight antibodies such as antibody fragments, modified products of antibodies, and the like. Furthermore, an antibody, which is prepared by fusing a Fc portion with an antibody fragment or a low molecular weight antibody, such as Fab, Fab', F(ab')$_2$, Fv, scFv (single chain Fv), or Diabody, so as to acquire ADCC activity, may also be used. In order to obtain such an antibody, a gene encoding such an antibody may be constructed, the gene may be then introduced into an expression vector, and the gene may be then allowed to express in a suitable host cell.

As a modified product of antibody, an antibody that is bound to various types of molecules such as polyethylene glycol (PEG) may be used. Moreover, it may also be possible to bind a radioisotope, a chemotherapeutic agent or the like to an antibody. A radiolabeled antibody is particularly useful. Such a modified product of antibody can be obtained by performing chemical modification on the obtained antibody. It is to be noted that a method of modifying antibodies is known to a person skilled in the art.

Since the antibody of the present invention exhibits high antibody-dependent cellular cytotoxicity, it can be used as a cytotoxic agent. The cytotoxic agent of the present invention may cause damage on, for example, cancer cells that express cadherin, by allowing it to come into contact with the cancer cells.

The cytotoxic agent of the present invention may comprise, as appropriate, a pharmaceutically acceptable carrier, an excipient, a diluent and other additives as well as the antibody of the present invention, as necessary. The cytotoxic agent of the present invention can be formulated in the form of an injection, for example. The applied dose of the cytotoxic agent of the present invention depends on the degree of symptoms, age and body weight of a patient, an administration method, and the like. The applied dose is generally within the range from approximately 10 ng/kg of body weight to approximately 100 mg/kg of body weight, in terms of the weight of an antibody as an active ingredient.

The present invention will be more specifically described in the following examples. However, these examples are not intended to limit the scope of the present invention.

EXAMPLES

Example 1

Establishment of CDH3-Expressing CHO Cell Line

In order to obtain a cell line used in the screening of an anti-CDH3 antibody, CHO cells that expressed full-length CDH3 were established.
(1) Preparation of Expression Vector for CDH3 Gene In order to insert full-length human CDH3 DNA shown in SEQ ID NO: 1 into a mammalian expression vector pEF4/myc-HisB (Invitrogen), the DNA was treated with two types of restriction enzymes KpnI (Takara Bio Inc.) and XbaI (Takara Bio Inc.) at 37° C. for 1 hour, and it was then inserted into pEF4/myc-HisB treated with the same KpnI and XbaI according to an ordinary method using T4 DNA ligase (Promega), so as to obtain an expression vector pEF4-CDH3-myc-His.
(2) Achievement of CDH3 Stably Expressing Cell Line In accordance with the protocols of FuGENE (registered trademark) 6 transfection reagent (Roche Diagnostics), on the day before transfection, CHO cells (8×10$^5$ cells) were inoculated on a dish with a diameter of 10 cm, and they were then cultured overnight. Thereafter, 8 μg of the expression vector pEF4-CDH3-myc-His and 16 μL of the FuGENE 6 reagent were mixed into 400 μL a serum-free RPMI 1640 medium (SIGMA-ALDRICH), and the mixture was then left at room temperature for 15 minutes. Thereafter, the mixture was added to the cell culture solution, so as to carry out transfection. Two days after the transfection, using a selective reagent (Zeocin (registered trademark)), cloning was carried out according to a limiting dilution method.

Figure 3:
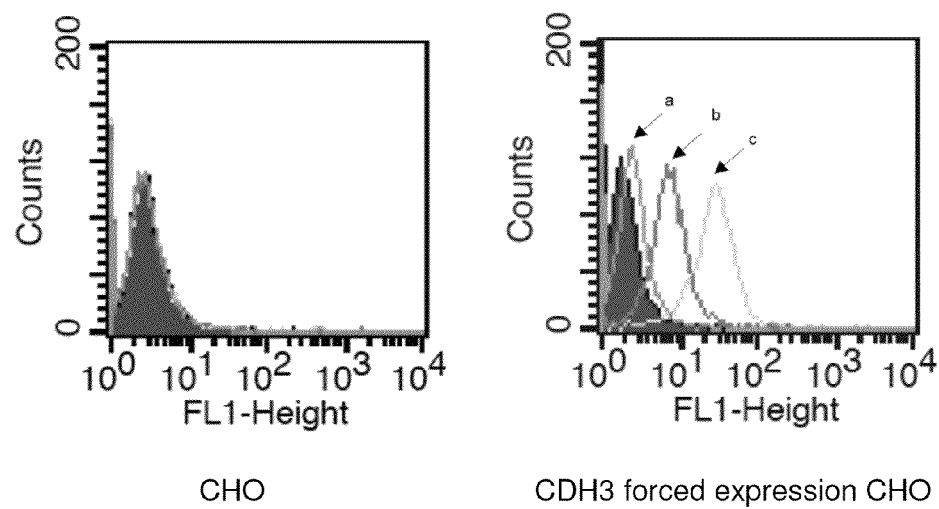
FIG. 3 shows the results of a flow cytometry, in which a human CDH3 forced expression cell line was allowed to react with a commercially available anti-human CDH3 antibody. A: CDH3 forced expression CHO cells; B: CHO cells; a: 0.01 µg/ml anti-CDH3 antibody; b: 0.1 µg/ml anti-CDH3 antibody; and c: 1 µg/ml anti-CDH3 antibody.

Clones of full-length CDH3-expressing CHO cells were selected according to a Western blot method using an anti-c-Myc monoclonal antibody (SANTA CRUZ BIOTECHNOLOGY). As a result, there was obtained a full-length CDH3-expressing CHO cell line (EXZ1501) which provided a high expression level of CDH3 and was able to grow favorably. The measurement results of a flow cytometry, in which the above-mentioned cell line was allowed to react with a commercially available anti-CDH3 antibody (R & D SYSTEMS), are shown in FIG. 3.

Example 2

Preparation of Soluble CDH3 Antigen

A soluble CDH3 (sCDH3) protein, in which its C-terminal transmembrane region and the subsequent regions were deleted, was prepared to be used as an immunogen in the production of an anti-CDH3 antibody.

(1) Preparation of Expression Vector for Soluble CDH3 Antigen

Using full-length CDH3 cDNA as a template, a PCR reaction was carried out employing a forward primer (SEQ ID NO. 7: CGCGGTACCATGGGGCTCCCTCGT (hCDH3 Full FW)) and a reverse primer (SEQ ID NO. 8: CCGTCTAGATAACCTCCCTTCCAGGGTCC (hCDH3 Solb RV)) that had been designed to amplify a region corresponding to a CDH3 extracellular region (which corresponds to 1-654 of SEQ ID NO: 2; hereinafter referred to as sCDH3 cDNA). KOD-Plus (Toyobo Co., Ltd.) was used in the reaction, and the reaction was carried out under reaction conditions consisting of 30 cycles of 94° C.—15 seconds, 55° C.—30 seconds and 68° C.—90 seconds.

Thereafter, a gel fragment containing an approximately 2.0 kbp band that was a size of interest was cut out in agarose gel electrophoresis, and using QIA (registered trademark) quick Gel Extraction Kit (QIAGEN), sCDH3 cDNA of interest was obtained.

In order to insert this sCDH3 cDNA into an expression vector pEF4/myc-HisB, the DNA was treated with two types of restriction enzymes KpnI and XbaI, and it was then inserted into pEF4/myc-HisB treated with the same KpnI and XbaI according to an ordinary method using T4 DNA ligase, so as to obtain an expression vector pEF4-sCDH3-myc-His.

(2) Expression of Soluble CDH3 Protein

In accordance with the protocols of the FuGENE 6 transfection reagent, on the day before transfection, CHO cells ($8 \times 10^5$ cells) were inoculated on a dish with a diameter of 10 cm, and they were then cultured overnight. Thereafter, 8 µg of the expression vector pEF4-sCDH3-myc-His and 16 µL of the FuGENE 6 reagent were mixed into 400 µL of a serum-free RPMI 1640 medium, and the mixture was then left at room temperature for 15 minutes. Thereafter, the mixture was added to the cell culture solution, so as to carry out transfection. Two days after the transfection, using a selective reagent (Zeocin), cloning was carried out according to a limiting dilution method.

Soluble CDH3-expressing CHO cells were selected according to a Western blot method using an anti-c-Myc monoclonal antibody (SANTA CRUZ BIOTECHNOLOGY). It was attempted to select a cell line, which secreted a large amount of soluble CDH3 into the culture supernatant and which was able to grow favorably. As a result, a soluble CDH3-expressing CHO cell line (EXZ1702) was obtained. Using three roller bottles each having a culture area of 1,500 cm$^2$, the selected soluble CDH3-expressing CHO cell line (EXZ1702) was cultured for 72 hours in 333 mL of a serum-free medium CHO-S-SFM-II (Invitrogen) per roller bottle. Thereafter, a culture supernatant was recovered. A soluble CDH3 protein was obtained from the recovered culture supernatant according to affinity chromatography using HisTrap (registered trademark) HP column (GE Healthcare Biosciences) and gel filtration chromatography using Superdex (registered trademark) 200 pg column (GE Healthcare Biosciences).

Example 3

Production of Anti-CDH3 Monoclonal Antibody (1) Preparation of Monoclonal Antibody Using Soluble CDH3 Protein as Immunogen 50 µg of a soluble CDH3 protein dissolved in a normal saline and Titer-MAX Gold (registered trademark) (Titer-Max) were mixed at equal volume. The obtained mixture was injected into the abdominal cavity and subcutis of an MRL/lpr mouse (Japan SLC, Inc.) so as to carry out initial immunization. The second immunization and the subsequent immunizations were carried out by mixing a soluble CDH3 protein (protein amount: 25 µg) that had been prepared in the same manner as described above with Titer-MAX gold and then injecting the obtained mixture into the abdominal cavity and subcutis of the mouse. Three days after the final immunization, splenic cells were aseptically prepared from the mouse, and the splenic cells were then fused with mouse myeloma cells SP2/O-Ag14 or P3-X63-Ag8.653 according to an ordinary method (polyethylene glycol method).

(2) Selection of Anti-CDH3 Antibody-Producing Hybridomas

An anti-CDH3 antibody was selected by flow cytometry using a CHO cell line (EXZ1501) expressing full-length CDH3.

Specifically, the CHO cell line (EXZ1501) that expressed full-length CDH3 was treated with 2 mM EDTA-PBS, so that it was removed from the culture plate. Thereafter, the cells were suspended in a FACS solution to a concentration of $1 \times 10^6$ cells/mL. This cell suspension was inoculated on a 96-well plate to a concentration of 50 µL/well, and a culture supernatant of hybridomas was then added thereto, so that they were reacted at 4° C. for 60 minutes. Thereafter, the reaction solution was washed with a FACS solution (200 µL/well) two times, and AlexaFluor 488-labeled anti-mouse IgG-goat F(ab')$_2$ (Invitrogen) was added to the resultant. Then, the mixture was reacted at 4° C. for 30 minutes. Thereafter, the reaction solution was washed with a FACS solution two times, and it was then subjected to flow cytometry, so as to select hybridomas that were strongly reacted with the CDH3-expressing CHO cells.

Figure 4:
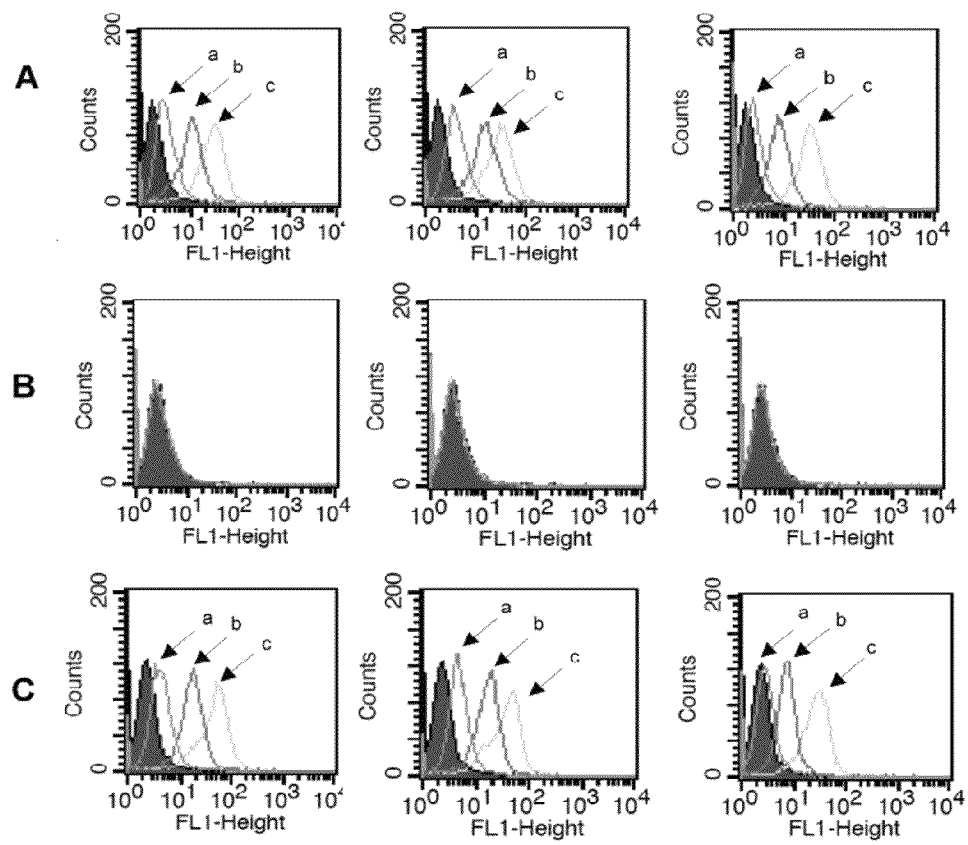
FIG. 4 shows the results of a typical flow cytometry regarding the obtained three antibody cases and each cell line. A: CDH3 forced expression CHO cells; B: CHO cells; C: lung cancer-derived cell line NCI-H358; a: 0.01 µg/ml anti-CDH3 antibody; b: 0.1 µg/ml anti-CDH3 antibody; and c: 1 µg/ml anti-CDH3 antibody.

The results of typical reactions of the antibody obtained from the aforementioned hybridomas with CDH3-expressing CHO cells (EXZ1501), with CHO cells as a parent cell line, and with cancer cells NCI-H358 that had been confirmed to express CDH3 at a high level, are shown in FIG. 4. All of the selected hybridomas were confirmed to react with the CDH3-expressing CHO cells (EXZ1501) and with the NCI-H358, but not to react with the CHO cells.

Example 4

Measurement of Antibody-Dependent Cellular Cytotoxic (ADCC) Activity of anti-CDH3 Antibody ADCC activity was measured by a method comprising allowing an antibody to act on radiolabeled target cells in the presence of effector cells and then measuring the released radioactivity.

(1) Preparation of Effector Cells

Bone-marrow cells were collected from the femur of a C3H/HeJ Jcl mouse (8-week-old, male, CLEA Japan, Inc.), and the cells were then prepared to a concentration of $2 \times 10^6$ cells/mL in a 10% FBS-containing RPMI1640 medium. Thereafter, the cells were cultured for 6 days in the presence of 50 ng/mL human IL-2 (PEPROTECH) and 10 ng/mL mouse GM-CSF (PEPROTECH). On the day of measurement, the cells were recovered and were then washed with a 10% FBS-containing HAM medium, so as to prepare an effector cell solution.

(2) Preparation of Target Cells

As target cells, full-length CDH3-expressing CHO cells (EXZ1501) were used. The cells were removed from a plate, and were then suspended in a 10% FBS-containing HAM medium to a concentration of $1\times10^7$ cells/mL. Then, $^{51}$Cr was added to the suspension to a final concentration of 150 µCi. The thus obtained mixture was cultured in a 5% $CO_2$ incubator at 37° C. for 1.5 hours. The resultant cells were washed with a medium twice, and a 10% FBS-containing HAM medium was then added thereto. Thereafter, the cells were inoculated on a 96-well U-bottom plate (NUNC) to a concentration of $1\times10^4$ cells/mL, so as to prepare target cells.

(3) Measurement of ADCC Activity

An antibody solution, which had been prepared to have a concentration of each of 0.001, 0.01, 0.1 and 1 µg/mL, was dispensed in 50 µL/well into the target cells. The obtained mixture was incubated at room temperature for 15 minutes. Thereafter, 100 µL of the effector cells ($1\times10^5$ cells/well) was dispensed therein, and the obtained mixture was then cultured in a $CO_2$ incubator for 4 hours. Thereafter, a culture supernatant was recovered, and radioactivity in 100 µL of the culture supernatant was measured with a scintillation counter.

Cytotoxicity was obtained by the following formula.

Cytotoxicity(%)=(A−B)/(B−C)×100

A: the radioactivity value (cpm) of each antibody-added well
B: the radioactivity value (cpm) of a well, in which 100 µL of a 2% NP40 solution and 50 µL of a 10% FBS-containing RPMI medium have been added to the target cells
C: the radioactivity value (cpm) of a well, in which 150 µL of a 10% FBS-containing medium comprising the effector cells has been added to the target cells The test was carried out by measuring ADCC activity according to a triplicate assay, and cytotoxicity (%) was calculated based on the obtained mean value.

Figure 5:
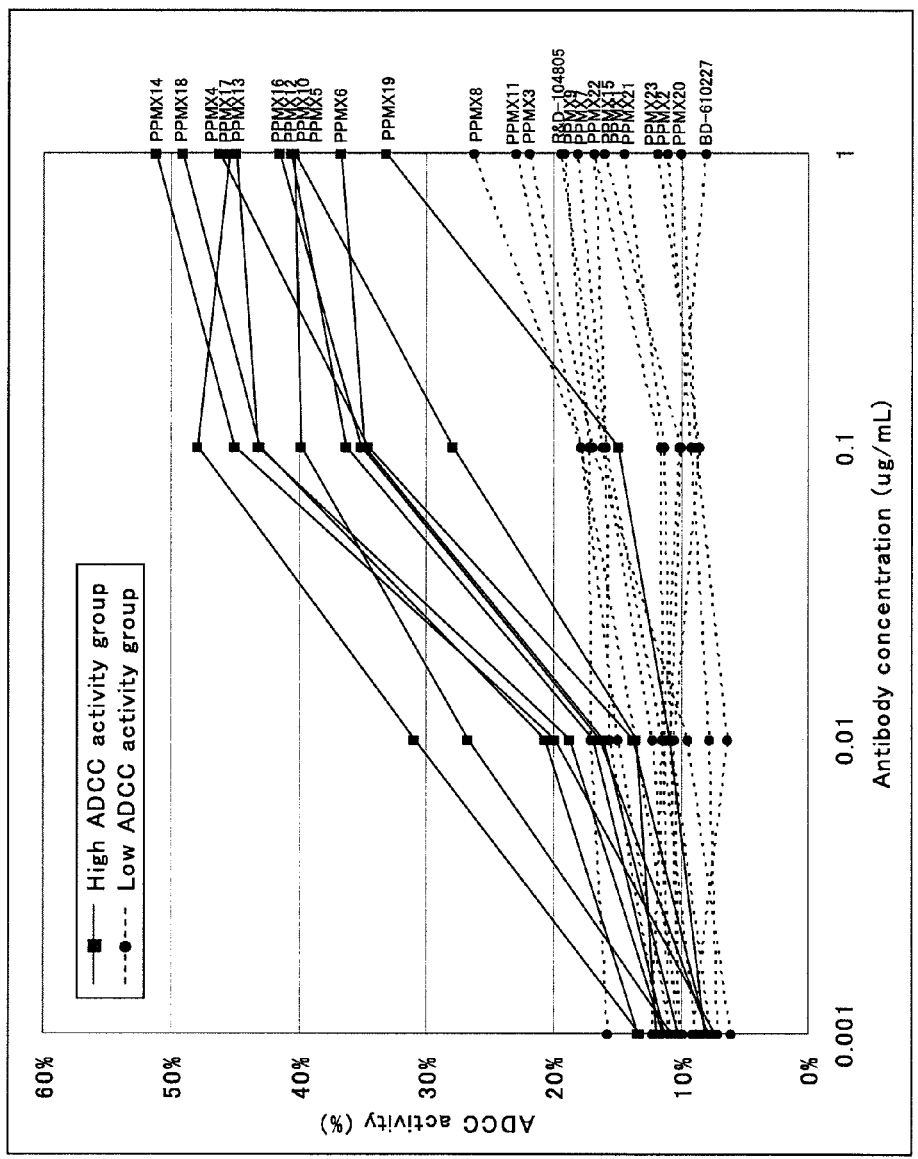
FIG. 5 shows the ADCC activity of each antibody.

The test results are shown in Table 1 and FIG. 5. An antibody group having particularly strong ADCC activity was found among antibodies having ADCC activity. Antibodies wherein ADCC activity at an antibody concentration of 1 µg/mL was 30% or more, were defined as a high ADCC activity group. Antibodies wherein ADCC activity at the same antibody concentration was less than 30%, were defined as a low ADCC activity group.

TABLE 1

| Antibody | Subtype | 0.001 | 0.01 | 0.1 | 1 | Evaluation* |
|---|---|---|---|---|---|---|
| PPMX3 | IgG1 | 6% | 9% | 17% | 22% | W |
| PPMX9 | IgG1 | 16% | 17% | 17% | 19% | W |
| PPMX11 | IgG1 | 11% | 15% | 18% | 23% | W |
| PPMX15 | IgG1 | 12% | 16% | 16% | 17% | W |
| R&D-104805 | IgG1 | 10% | 12% | 16% | 19% | W |
| BD-610227 | IgG1 | 11% | 11% | 10% | 8% | W |
| PPMX1 | IgG1 | 8% | 11% | 10% | 16% | W |
| PPMX10 | IgG1 | 11% | 27% | 40% | 40% | S |
| PPMX13 | IgG1 | 11% | 19% | 43% | 45% | S |
| PPMX18 | IgG1 | 13% | 21% | 43% | 49% | S |
| PPMX14 | IgG1 | 7% | 20% | 45% | 51% | S |
| PPMX4 | IgG1 | 8% | 14% | 35% | 46% | S |
| PPMX5 | IgG1 | 12% | 13% | 28% | 40% | S |
| PPMX6 | IgG1 | 10% | 16% | 35% | 37% | S |
| PPMX16 | IgG1 | 8% | 16% | 35% | 42% | S |
| PPMX17 | IgG1 | 13% | 31% | 48% | 45% | S |
| PPMX2 | IgG2a | 7% | 8% | 9% | 11% | W |
| PPMX21 | IgG2a | 10% | 11% | 11% | 14% | W |
| PPMX7 | IgG2a | 9% | 11% | 16% | 18% | W |
| PPMX8 | IgG2a | 10% | 14% | 18% | 26% | W |
| PPMX20 | IgG2a | 9% | 6% | 9% | 10% | W |
| PPMX23 | IgG2a | 10% | 10% | 9% | 12% | W |
| PPMX22 | IgG2a | 12% | 11% | 12% | 17% | W |
| PPMX12 | IgG2a | 11% | 17% | 36% | 41% | S |
| PPMX19 | IgG2b | 8% | 11% | 15% | 33% | S |
| Negative Ab1 | IgG1 | 10% | 10% | 9% | 8% | — |
| Negative Ab2 | IgG2a | 12% | 13% | 13% | 11% | — |

R & D-104805 indicates a commercially available CDH3 antibody (R & D SYSTEMS).
BD-610227 indicates another commercially available CDH3 antibody (BD BIOSCIENCES).
Negative Ab1 and Ab2 indicate antibodies that recognize antigens irrelevant to CDH3.
*S: high ADCC activity (30% or more at an antibody concentration of 1 µg/mL) W: low ADCC activity (less than 30% at an antibody concentration of 1 µg/mL)
Hybridoma PPMX12 that produces antibody PPMX12 was deposited under the terms of the Budapest Treaty with the International Patent Organism Depositary, the National Institute of Technology and Evaluation, an Independent Administrative Institution under the Ministry of Economy, Trade and Industry (2-5-8, Kazusa Kamatari, Kisarazu-shi, Chiba-ken, Japan, postal code: 292-0818), under accession No. NITE BP-865 on Jan. 20, 2010.

Example 5

Figure 6:
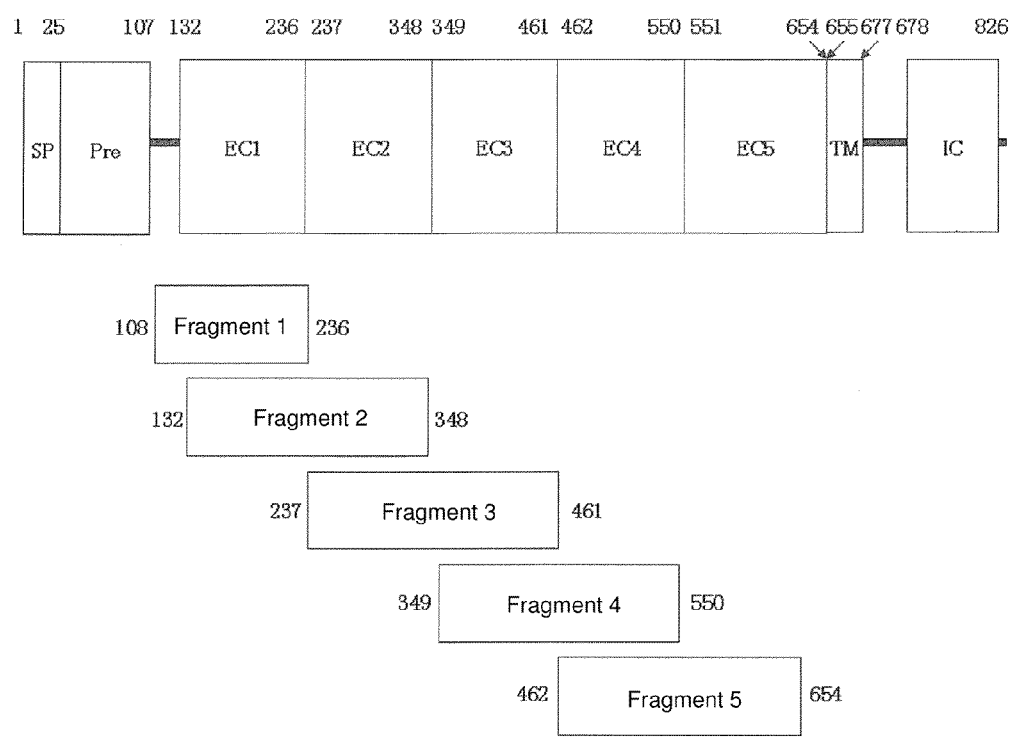
FIG. 6 shows the correlation of partial-length CDH3 protein fragments 1 to 5 with a CDH3 extracellular region.

Classification of Epitopes of Anti-CDH3 Monoclonal Antibody with Use of Partial-Length CDH3-Expressing Protein The obtained anti-CDH3 antibody epitopes were classified by a Western blot method with CDH3 partial sequence expression products. As such CDH3 partial sequence expression products, fragments 1 to 5 were designed, so that the sequences of the fragments could be sufficiently overlapped (FIG. 6).

(1) Production of Expression Vector for Partial-Length CDH3 Protein

Using the full-length CDH3 cDNA of Example 1 as a template, a PCR reaction was carried out employing the aftermentioned primer sets. Using iProof High Fidelity DNA Polymerase (Bio-Rad), the reaction was carried out under reaction conditions consisting of 35 cycles of 98° C.—10 seconds, 60° C.—10 seconds, and 72° C.—30 seconds. Thereafter, gel containing a band with a size near the size of interest was cut out in agarose gel electrophoresis, and using QIA (registered trademark) quick Gel Extraction Kit, a CDH3 cDNA fragment of interest was obtained.

In order to insert this CDH3 cDNA fragment into an *Escherichia coli* expression vector pCold (registered trademark) TF (Takara Bio Inc.), the fragment was treated with two types of restriction enzymes KpnI and XbaI, and it was then inserted into pCold TF treated with the same KpnI and XbaI according to an ordinary method using T4 DNA ligase, so as to obtain an expression vector for expressing each fragment.

Using the following primer sets, PCR reactions were carried out, so as to obtain each fragment.

```
Fragment 1 (positions 108-236 of SEQ ID NO: 2)
Forward primer:
                                        (SEQ ID NO: 9)
TATGGAGCTCGGTACCGATTGGGTGGTTGCTCCAATATCTG Reverse primer:
                                        (SEQ ID NO: 10)
AGATTACCTATCTAGACTACTGCATCACAGAAGTACCTGGTAGG Fragment 2 (positions 132-348 of SEQ ID NO: 2)
Forward primer:
                                        (SEQ ID NO: 11)
TATGGAGCTCGGTACCAAGTCTAATAAAGATAGAGACACCAAG Reverse primer:
                                        (SEQ ID NO: 12)
AGATTACCTATCTAGACTACCTCTGCACCTCATGGCCCACTGCATTCTCA
```

-continued

Fragment 3 (positions 237-461 of SEQ ID NO: 2)
Forward primer:
(SEQ ID NO: 13)
TATGGAGCTCGGTACCGTGACAGCCACGGATGAGGATGATG Reverse primer:
(SEQ ID NO: 14)
AGATTACCTATCTAGACTAGACACACACAGGCTCCCCAGTG Fragment 4 (positions 349-550 of SEQ ID NO: 2)
Forward primer:
(SEQ ID NO: 15)
TATGGAGCTCGGTACCCTGACGGTCACTGATCTGGACG Reverse primer:
(SEQ ID NO: 16)
AGATTACCTATCTAGACTAGGGCTCAGGGACTGGGCCATGGTCATTG Fragment 5 (positions 462-654 of SEQ ID NO: 2)
Forward primer:
(SEQ ID NO: 17)
TATGGAGCTCGGTACCTACACTGCAGAAGACCCTGACAAGG Reverse primer:
(SEQ ID NO: 18)
AGATTACCTATCTAGACTAACCTCCCTTCCAGGGTCCAGGGCAGGTTTCG (2) Expression of Partial-Length CDH3 Protein Using the expression vector of the CDH3 fragment described in (1) above, *Escherichia coli* Rossetta (registered trademark) 2 (Merck) was transformed according to an ordinary method, and the transformant was then cultured in a LB medium. When the absorbance at 600 nm became 0.4, the culture product was cooled on ice for 30 minutes. Then, the concentration of isopropyl-β-thiogalactopyranoside (IPTG) was set at 0.5 mM, and the cells was cultured at 20° C. for 18 hours, and the resultant was then recovered.

The expression of a partial-length CDH3 protein was confirmed by electrophoresing the culture solution of the *Escherichia coli*, subjecting the resultant to a Western blot method using an anti-Penta-His antibody (QIAGEN), and then confirming the presence of a band in a predicted position.

Figure 7:
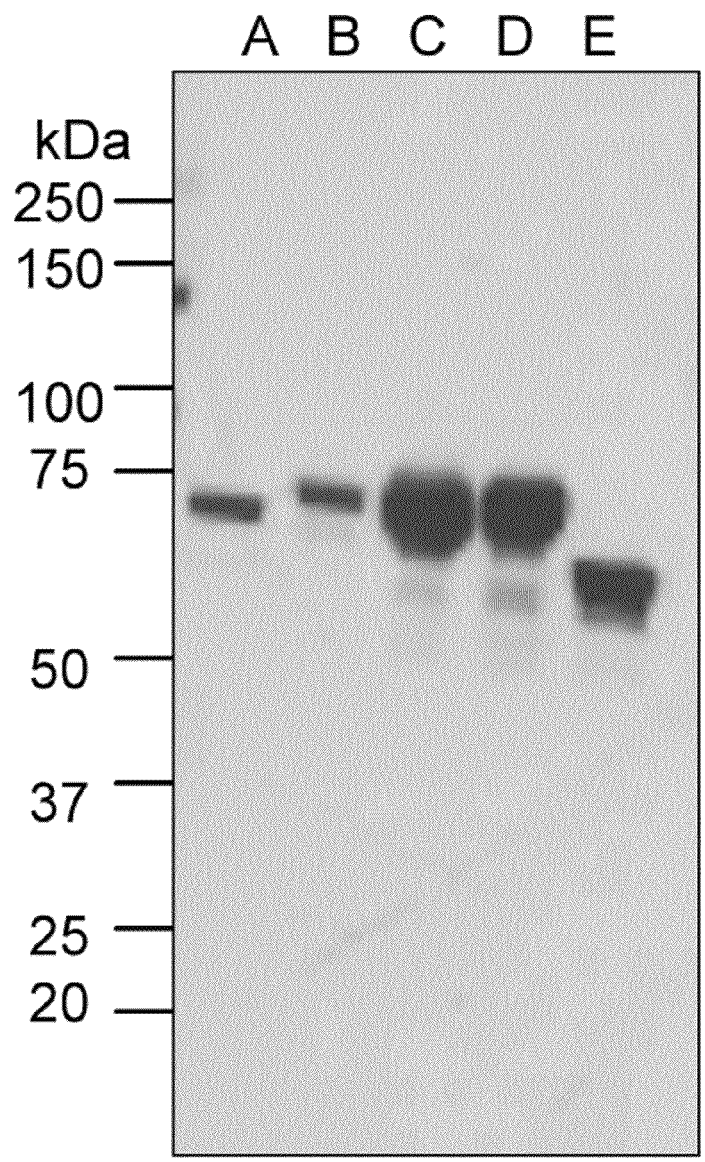
FIG. 7 shows the results of expression of partial-length CDH3 proteins. A: fragment 1; B: fragment 2; C: fragment 3; D: fragment 4; and E: fragment 5.

Specifically, an electrophoretic buffer was added to the above-described *Escherichia coli* culture solution in an amount of 1/10 of the culture solution, and the thus mixed solution was then charged to 5%-20% gradient gel (Bio-Rad) under reductive conditions, followed by performing electrophoresis. Thereafter, the resultant was transferred on Immobilon (registered trademark) P membrane (Millipore). The transfer membrane was lightly washed with TBS-T (0.05% Tween (registered trademark) 20, TBS), and it was then shaken in 40% BSA-containing TBS for 1 hour. Thereafter, each anti-CDH3 antibody that had been diluted with TBS-T containing 10% Block Ace (registered trademark) (Snow Brand Milk Products Co., Ltd.) was added to the resultant, and the obtained mixture was then shaken for 1 hour. Thereafter, the reaction product was washed with TBS-T, and a HRP-anti-mouse IgG antibody (GE Healthcare Biosciences) diluted with 10% Block Ace-containing TBS-T was added thereto, followed by shaking the obtained mixture for 1 hour. Subsequently, the reaction product was washed with TBS-T. Using ECL (registered trademark)-Plus (GE Healthcare Biosciences), color development was detected with X-ray film RX-u (Fujifilm Corporation) in accordance with the instructions provided by the manufacturer. The obtained results are shown in FIG. 7.

Figure 8:
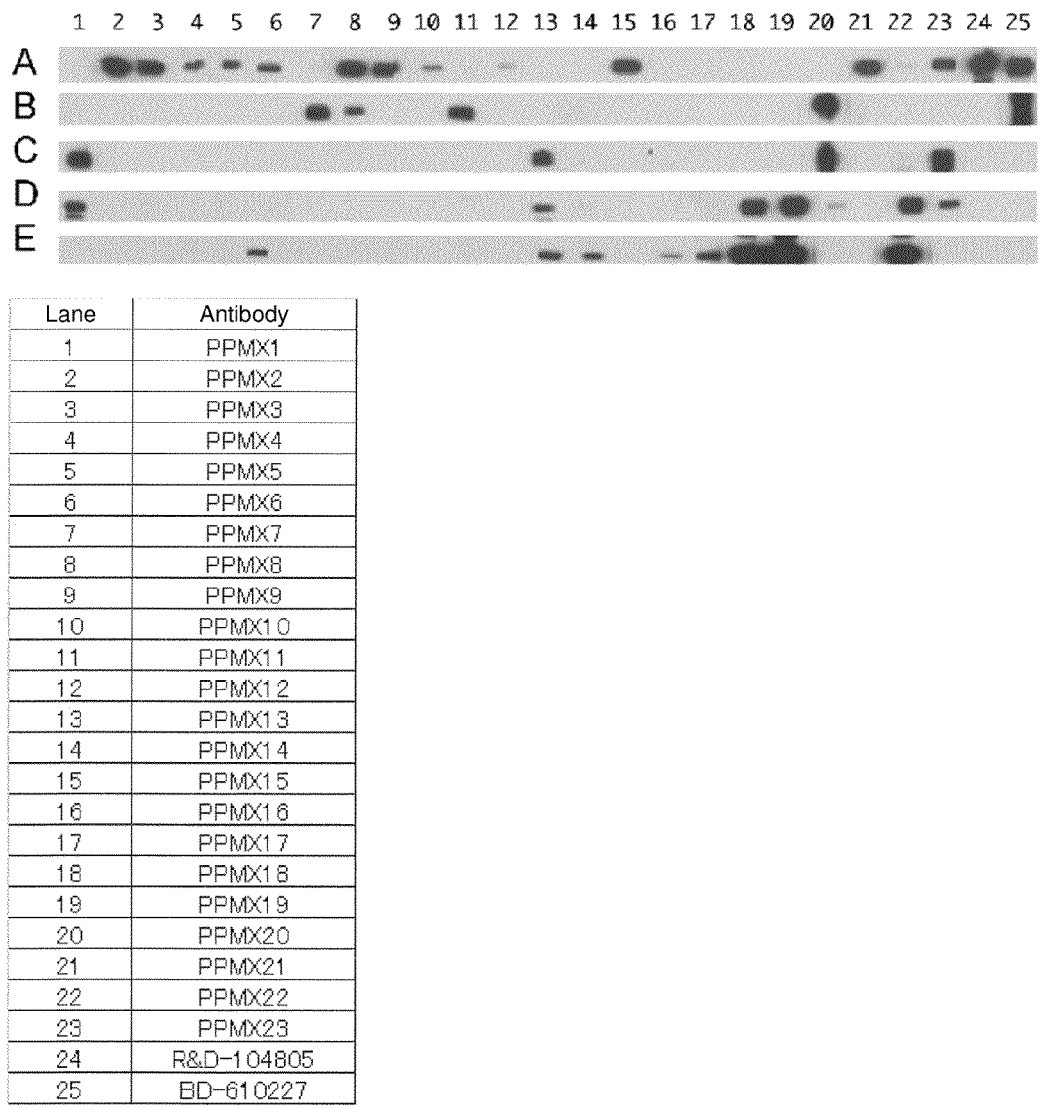
FIG. 8 shows the reaction of partial-length CDH3 proteins with each antibody according to a Western blot method. A: fragment 1; B: fragment 2; C: fragment 3; D: fragment 4; and E: fragment 5.

(3) Classification of Antibody Epitopes Using CDH3 Partial Sequence Expression Products The above-described *Escherichia coli* lysate, in which each partial-length CDH3 protein had been expressed, was charged to 5%-20% gradient gel (Bio-Rad) under reductive conditions, followed by performing electrophoresis. Thereafter, using a blotting device (Bio-Rad), the resultant was transferred on Immobilon P membrane (Millipore). The transfer membrane was lightly washed with TBS-T (0.05% Tween 20, TBS), and it was then shaken in 40% BSA-containing TBS for 1 hour. Thereafter, the membrane was cut at equal intervals in the form of straps, and each anti-CDH3 antibody that had been diluted with 10% Block Ace-containing TBS-T was added thereto. The obtained mixture was shaken for 1 hour. Thereafter, the reaction product was washed with TBS-T, and a HRP-anti-mouse IgG antibody (GE Healthcare Biosciences) diluted with 10% Block Ace-containing TBS-T was added thereto, followed by shaking the obtained mixture for 1 hour. Subsequently, the reaction product was washed with TBS-T. Using ECL (registered trademark)-Plus (GE Healthcare Biosciences), color development was detected with X-ray film RX-u (Fujifilm Corporation) in accordance with the instructions provided by the manufacturer. The obtained results are shown in FIG. 8.

Regions recognized by individual antibodies were determined based on the reactivity with each partial-length CDH3 protein (Table 2).

Correspondence relation with regions on the CDH3 sequence shown in SEQ ID NO: 2 that are recognized by individual antibodies is shown below.

Upstream region of EC1: positions 108-131
EC1: positions 132-236
EC2: positions 237-348
EC3: positions 349-461
EC4: positions 462-550
EC5: positions 551-654

TABLE 2

| Antibody | Subtype | Antibody concentration (μg/mL) | | | | Evaluation* | Recognized region |
|---|---|---|---|---|---|---|---|
| | | 0.001 | 0.01 | 0.1 | 1 | | |
| PPMX3 | IgG1 | 6% | 9% | 17% | 22% | W | Region upstream of EC1 |
| PPMX9 | IgG1 | 16% | 17% | 17% | 19% | W | Region upstream of EC1 |
| PPMX11 | IgG1 | 11% | 15% | 18% | 23% | W | EC1 |
| PPMX15 | IgG1 | 12% | 16% | 16% | 17% | W | Region upstream of EC1 |
| R&D-104805 | IgG1 | 10% | 12% | 16% | 19% | W | Region upstream of EC1 |
| BD-610227 | IgG1 | 11% | 11% | 10% | 8% | W | EC1 |
| PPMX1 | IgG1 | 8% | 11% | 10% | 16% | W | EC3 |
| PPMX10 | IgG1 | 11% | 27% | 40% | 40% | S | Region upstream of EC1 |
| PPMX13 | IgG1 | 11% | 19% | 43% | 45% | S | Border between EC3 and EC4 |
| PPMX18 | IgG1 | 13% | 21% | 43% | 49% | S | EC4 |
| PPMX14 | IgG1 | 7% | 20% | 45% | 51% | S | EC5 |

TABLE 2-continued

| Antibody | Subtype | Antibody concentration (µg/mL) | | | | Evaluation* | Recognized region |
|---|---|---|---|---|---|---|---|
| | | 0.001 | 0.01 | 0.1 | 1 | | |
| PPMX4 | IgG1 | 8% | 14% | 35% | 46% | S | Region upstream of EC1 |
| PPMX5 | IgG1 | 12% | 13% | 28% | 40% | S | Region upstream of EC1 |
| PPMX6 | IgG1 | 10% | 16% | 35% | 37% | S | Region upstream of EC1, or EC5 |
| PPMX16 | IgG1 | 8% | 16% | 35% | 42% | S | EC5 |
| PPMX17 | IgG1 | 13% | 31% | 48% | 45% | S | EC5 |
| PPMX2 | IgG2a | 7% | 8% | 9% | 11% | W | Region upstream of EC1 |
| PPMX21 | IgG2a | 10% | 11% | 11% | 14% | W | Region upstream of EC1 |
| PPMX7 | IgG2a | 9% | 11% | 16% | 18% | W | EC1 |
| PPMX8 | IgG2a | 10% | 14% | 18% | 26% | W | EC1 |
| PPMX20 | IgG2a | 9% | 6% | 9% | 10% | W | EC2 |
| PPMX23 | IgG2a | 10% | 10% | 9% | 12% | W | Region upstream of EC1, or EC3 |
| PPMX22 | IgG2a | 12% | 11% | 12% | 17% | W | EC4 |
| PPMX12 | IgG2a | 11% | 17% | 36% | 41% | S | Region upstream of EC1 |
| PPMX19 | IgG2b | 8% | 11% | 15% | 33% | S | EC4 |
| Negative Ab1 | IgG1 | 10% | 10% | 9% | 8% | — | — |
| Negative Ab2 | IgG2a | 12% | 13% | 13% | 11% | — | — |

R & D-104805 indicates a commercially available CDH3 antibody (R & D SYSTEMS).
BD-610227 indicates another commercially available CDH3 antibody (BD BIOSCIENCES).
Negative Ab1 and Ab2 indicate antibodies that recognize antigens irrelevant to CDH3.
*S: high ADCC activity (30% or more at an antibody concentration of 1 µg/mL) W: low ADCC activity (less than 30% at an antibody concentration of 1 µg/mL)

Example 6

Determination of Anti-CDH3 Monoclonal Antibody Epitopes Using Peptide Array

A peptide array (Replitope; manufactured by JPT Peptide Technologies) was applied to antibody PPMX13 that was considered to correspond to a boundary region in the above-described epitope determination using a partial-length CDH3-expressing protein, so that epitope determination was carried out more in detail.

Specifically, a region corresponding to the extracellular region of CDH3 (which corresponds to positions 108-563 of SEQ ID NO: 2) was shifted by every 13 residues from the N-terminus, while each initial residue was shifted by every two amino acid residues (that is, positions 108-120, 110-122, ... and 551-563), so as to synthesize peptides. The thus synthesized peptides were immobilized on a glass slide, and were then blocked by SuperBlock (PIERCE). The thus prepared product was used as a primary antibody, and it was allowed to react with antibodies as targets of epitope searching. The reaction product was washed with TBS-T three times, and detection was then carried out using an anti-mouse antibody (PIERCE) that had been fluorescently labeled with DyLight649. A primary antibody that had not been allowed to react with the antibody as a epitope searching target was used as a negative control in the measurement. The measurement results are shown in FIG. 9. Strong signals were observed in regions corresponding to positions 446-472 and 490-504 of the amino acid sequence of CDH3 shown in SEQ ID NO: 2, and these were assumed to be epitopes of the present antibody.

The correlation of ADCC activity in view of the results regarding the regions recognized by the antibodies, which were determined in Examples 5 and 6, was analyzed. As a result, it was found that antibodies having high ADCC activity were concentrated in an upstream region of EC1, the EC4 region and the EC5 region.

Example 7

Expression of CDH3 mRNA in Normal Tissues and Cancer Tissues

Figure 10:
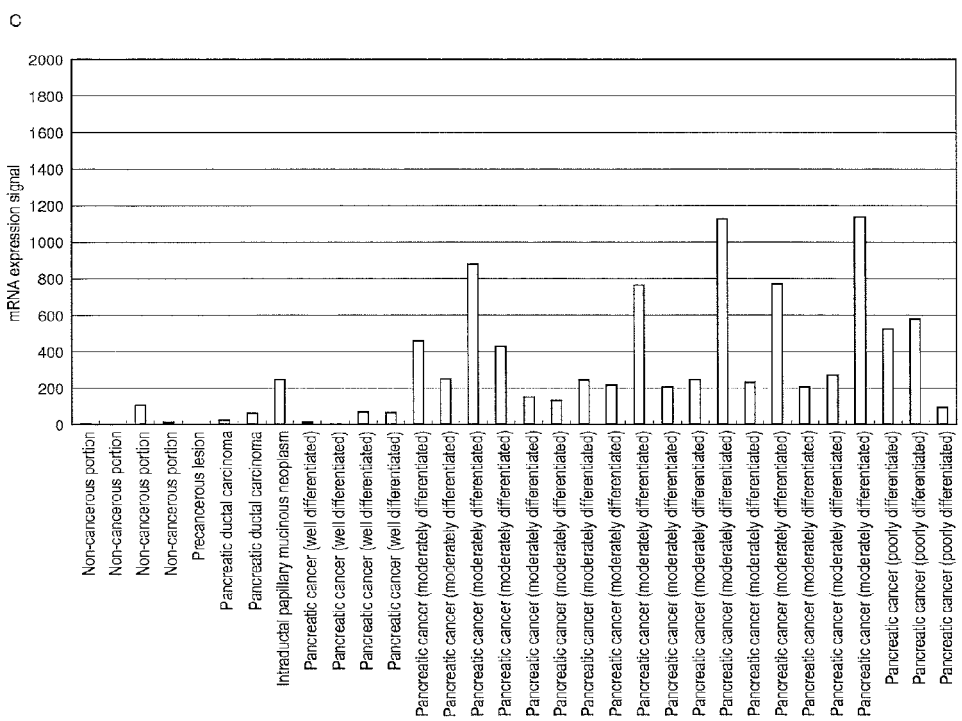
FIG. 10 shows the results of the mRNA expression of CDH3 in various types of tumor tissues. A: normal tissues; B: various types of cancer tissues; and C: differentiation degree of pancreatic cancer.

Samples were recovered from normal human tissues and various types of cancer tissues according to a Lase Capture Microdissection method. Total RNA was prepared from the recovered samples according to a common method using ISOGEN (Nippon Gene Co., Ltd.). 10 ng each of RNA was subjected to the analysis of gene expression using GeneChip U-133B (Affimetrix) in accordance with Expression Analysis Technical Manual (Affimetrix). The mean value of the expression scores of all genes was set at 100, and genes whose expression was increased in cancer cells were then searched. As a result, it was found that CDH3 was highly expressed in lung cancer, colon cancer, and pancreatic cancer (FIG. 10B). In addition, the expression of CDH3 mRNA in various types of pancreatic cancer tissues having different degrees of differentiation was studied. As a result, there were found tissues in which CDH3 was highly expressed, regardless of degree of differentiation (FIG. 10C).

Example 8

Expression of CDH3 Protein in Cancer Tissues by Immunohistochemical Staining

In order to confirm the expression of a CDH3 protein in cancer clinical samples, immunostaining was carried out using cancer sample tissue arrays.

As such cancer sample tissue arrays, pancreatic cancer (adenocarcinoma), lung cancer (adenocarcinoma), lung cancer (squamous-cell carcinoma) and colon cancer (adenocarcinoma), which were manufactured by Shanghai Outdo Biotech Co., Ltd.), were used.

Each tissue array slide was deparaffinized, and it was then activated with 10 mM Tris-1 mM EDTA (pH 9.0) at 95° C. for 40 minutes. Using a blocking reagent included with ENVISION+ Kit (Dako), endogenous peroxidase was inactivated, and the resultant was then reacted with anti-CDH3 antibody 610227 (BD BIOSCIENCES) and anti-HBs antibody Hyb- 3423 used as a negative control, in a concentration of 5 μg/mL at 4° C. overnight. After the antibody solution had been washed out, the resultant was reacted with a polymer secondary antibody reagent included with ENVISION+ Kit at room temperature for 30 minutes. Thereafter, color development was carried out using a coloring reagent included with ENVISION+ Kit, and nuclear staining was then carried out with a hematoxylin eosin solution.

Figure 11:
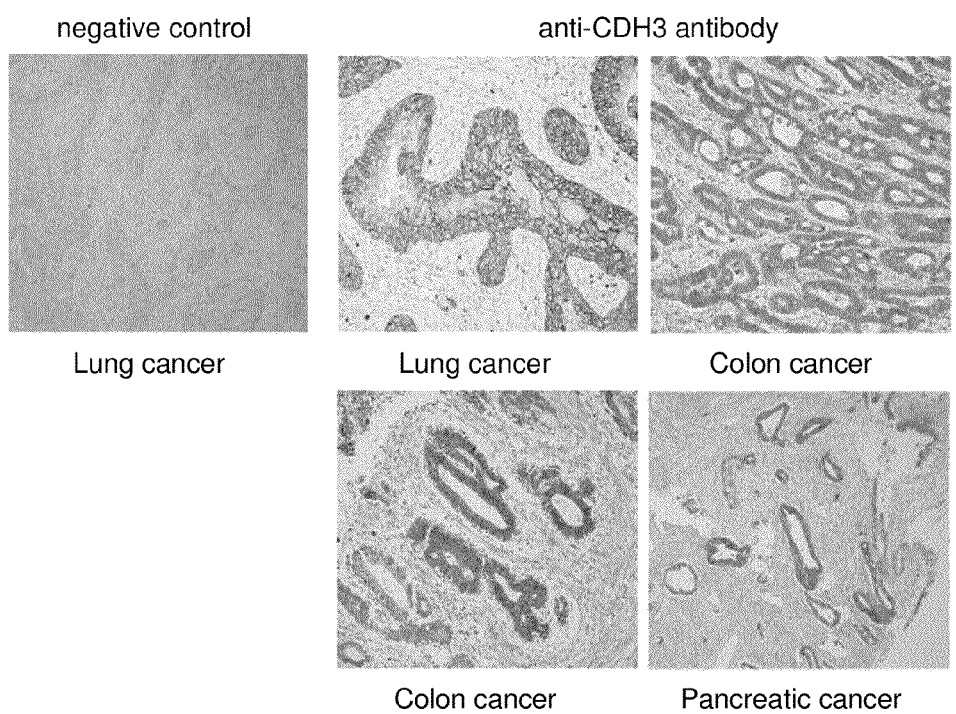
FIG. 11 shows the results of the expression of CDH3 in various types of tumor tissues.

The results are shown in FIG. 11. Cancer cells were stained with the anti-CDH3 antibody, and normal cells were not stained therewith.

Example 9

Antitumor Effects in Xenograft Models

The antitumor effect of an anti-CDH3 antibody was confirmed using xenografts, into which a human lung cancer-derived cell line NCI-H358, a human skin cancer-derived cell line A431, and a human pancreatic cancer-derived cell line PK-45P had been transplanted.

NCI-H358 and PK-45P were cultured in a 10% FBS-containing RPMI 1640 medium, whereas A431 was cultured in a 10% FBS-containing DMEM medium. Thereafter, each cell line was transplanted into the subcutis of the right ventral portion of each SCID mouse (female, 7-week-old, CLEA Japan), resulting in a concentration of $5 \times 10^6$ cells/mouse.

NCI-H358-transplanted mice were divided into six groups (n=8). A PPMX12-producing antibody was administered in a concentration of 0.01 mg/kg, 0.06 mg/kg, 0.3 mg, kg, or 1.5 mg/kg into the caudal vein of each mouse in each group. A RCB1205-producing antibody (anti-pertussis toxin mouse IgG antibody) used as a control was administered in a concentration of 7.5 mg/kg into the caudal vein of each mouse in each group. Administration was initiated at the time point in which the mean tumor diameter became 90 mm³, and the aforementioned antibody was administered twice a week (every 3 or 4 days) eight times in total.

PK-45P-transplanted mice were divided into two groups (n=8). A PPMX12-producing antibody was administered in a concentration of 7.5 mg/kg into the caudal vein of each mouse in each group. A RCB 1205-producing antibody (anti-pertussis toxin mouse IgG antibody) used as a control was administered in a concentration of 7.5 mg/kg into the caudal vein of each mouse in each group. Administration was initiated at the time point in which the mean tumor diameter became 120 mm³, and the aforementioned antibody was administered twice a week (every 3 or 4 days) seven times in total.

A431-transplanted mice were divided into two groups (n=8). A PPMX12-producing antibody was administered in a concentration of 7.5 mg/kg into the caudal vein of each mouse in each group. A RCB1205-producing antibody (anti-pertussis toxin mouse IgG antibody) used as a control was administered in a concentration of 7.5 mg/kg into the caudal vein of each mouse in each group. Administration was initiated at the time point in which the mean tumor diameter became 110 mm³, and the aforementioned antibody was administered twice a week (every 3 or 4 days) six times in total.

Figure 12:
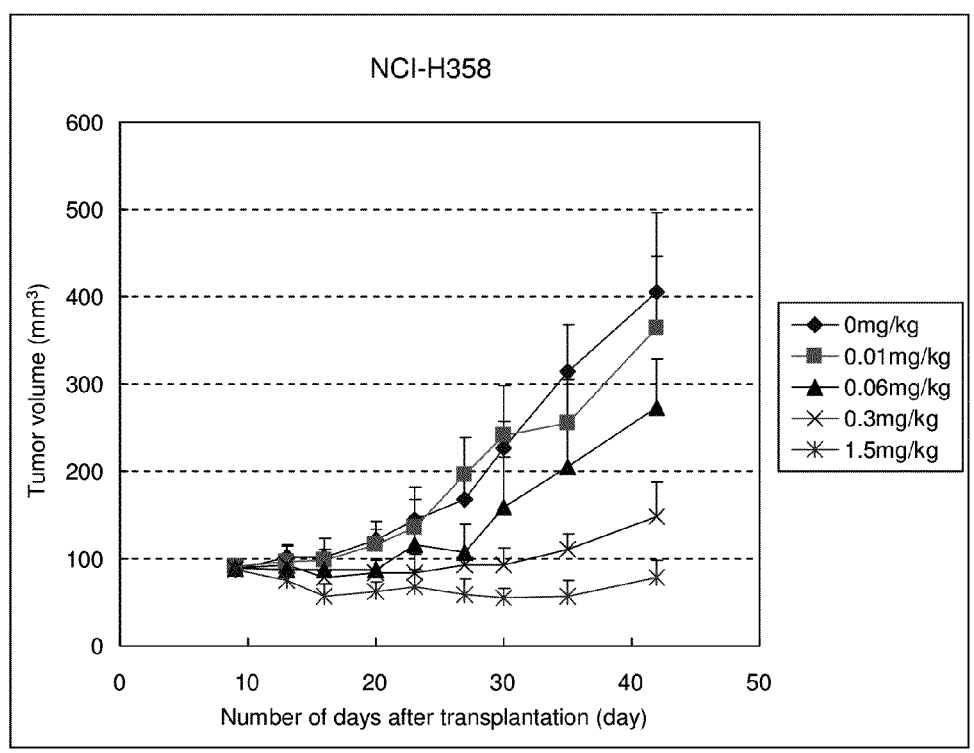
FIG. 12 shows the antitumor effect of PPMX12-producing antibody in a xenograft into which a human lung cancer-derived cell line NCI-H351 has been transplanted.
Figure 13:
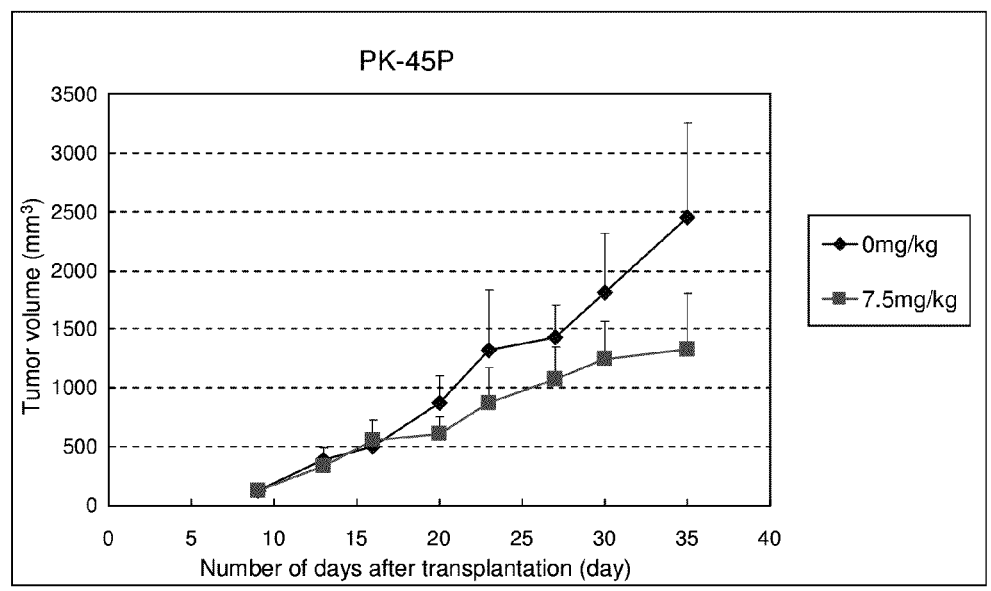
FIG. 13 shows the antitumor effect of PPMX12-producing antibody in a xenograft into which a human pancreatic cancer-derived cell line PK-45P has been transplanted.
Figure 14:
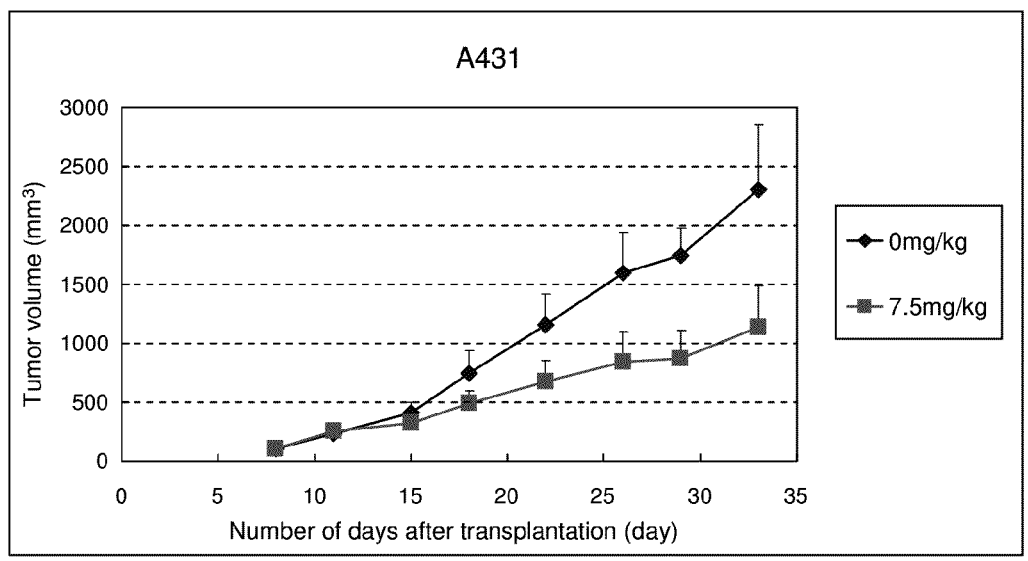
FIG. 14 shows the antitumor effect of PPMX12-producing antibody in a xenograft into which a human skin cancer-derived cell line A431 has been transplanted.

On the day of administration, a tumor size and a body weight were measured. After completion of the final administration, the mice were further observed for one week, and a body weight, a tumor size, and a tumor weight were measured. The results of each type of mouse were shown in FIGS. 12-14. The PPMX12-producing antibody exhibited antitumor activity in all of the tests. In addition, it was confirmed that antitumor effect was enhanced in a dose-dependent manner in the test using the NCI-H358-transplanted mice.

The invention claimed is:

1. An antibody which is produced from the hybridoma PPMX12, Accession No. NITE BP-865.

2. A chimeric antibody which is obtained from the antibody of claim 1.

3. A humanized antibody which is obtained from the antibody of claim 1.

4. A cytotoxic agent which comprises the antibody of claim 1.

5. A cytotoxic agent which comprises the antibody of claim 1.

6. A cytotoxic agent which comprises the antibody of claim 3.

7. A hybridoma PPMX12, Accession No. NITE BP-865.

* * * * *

SEQUENCE LISTING

<160> NUMBER OF SEQ ID NOS: 18

<210> SEQ ID NO 1
<211> LENGTH: 2490
<212> TYPE: DNA
<213> ORGANISM: human
<220> FEATURE:
<221> NAME/KEY: CDS
<222> LOCATION: (1)..(2490)

<400> SEQUENCE: 1

```
atg ggg ctc cct cgt gga cct ctc gcg tct ctc ctc ctt ctc cag gtt        48
Met Gly Leu Pro Arg Gly Pro Leu Ala Ser Leu Leu Leu Leu Gln Val
1               5                   10                  15 tgc tgg ctg cag tgc gcg gcc tcc gag ccg tgc cgg gcg gtc ttc agg        96
Cys Trp Leu Gln Cys Ala Ala Ser Glu Pro Cys Arg Ala Val Phe Arg
            20                  25                  30 gag gct gaa gtg acc ttg gag gcg gga ggc gcg gag cag gag ccc ggc       144
Glu Ala Glu Val Thr Leu Glu Ala Gly Gly Ala Glu Gln Glu Pro Gly
        35                  40                  45 cag gcg ctg ggg aaa gta ttc atg ggc tgc cct ggg caa gag cca gct       192
Gln Ala Leu Gly Lys Val Phe Met Gly Cys Pro Gly Gln Glu Pro Ala
    50                  55                  60 ctg ttt agc act gat aat gat gac ttc act gtg cgg aat ggc gag aca       240
Leu Phe Ser Thr Asp Asn Asp Asp Phe Thr Val Arg Asn Gly Glu Thr
65                  70                  75                  80 gtc cag gaa aga agg tca ctg aag gaa agg aat cca ttg aag atc ttc       288
Val Gln Glu Arg Arg Ser Leu Lys Glu Arg Asn Pro Leu Lys Ile Phe
```

-continued

```
                    85                      90                      95
cca tcc aaa cgt atc tta cga aga cac aag aga gat tgg gtg gtt gct    336
Pro Ser Lys Arg Ile Leu Arg Arg His Lys Arg Asp Trp Val Val Ala
            100                     105                     110 cca ata tct gtc cct gaa aat ggc aag ggt ccc ttc ccc cag aga ctg    384
Pro Ile Ser Val Pro Glu Asn Gly Lys Gly Pro Phe Pro Gln Arg Leu
            115                     120                     125 aat cag ctc aag tct aat aaa gat aga gac acc aag att ttc tac agc    432
Asn Gln Leu Lys Ser Asn Lys Asp Arg Asp Thr Lys Ile Phe Tyr Ser
        130                     135                     140 atc acg ggg ccg ggg gca gac agc ccc cct gag ggt gtc ttc gct gta    480
Ile Thr Gly Pro Gly Ala Asp Ser Pro Pro Glu Gly Val Phe Ala Val
145                     150                     155                 160 gag aag gag aca ggc tgg ttg ttg aat aag cca ctg gac cgg gag        528
Glu Lys Glu Thr Gly Trp Leu Leu Leu Asn Lys Pro Leu Asp Arg Glu
                    165                     170                     175 gag att gcc aag tat gag ctc ttt ggc cac gct gtg tca gag aat ggt    576
Glu Ile Ala Lys Tyr Glu Leu Phe Gly His Ala Val Ser Glu Asn Gly
                180                     185                     190 gcc tca gtg gag gac ccc atg aac atc tcc atc atc gtg acc gac cag    624
Ala Ser Val Glu Asp Pro Met Asn Ile Ser Ile Ile Val Thr Asp Gln
            195                     200                     205 aat gac cac aag ccc aag ttt acc cag gac acc ttc cga ggg agt gtc    672
Asn Asp His Lys Pro Lys Phe Thr Gln Asp Thr Phe Arg Gly Ser Val
        210                     215                     220 tta gag gga gtc cta cca ggt act tct gtg atg cag gtg aca gcc acg    720
Leu Glu Gly Val Leu Pro Gly Thr Ser Val Met Gln Val Thr Ala Thr
225                     230                     235                 240 gat gag gat gat gcc atc tac acc tac aat ggg gtg gtt gct tac tcc    768
Asp Glu Asp Asp Ala Ile Tyr Thr Tyr Asn Gly Val Val Ala Tyr Ser
                    245                     250                     255 atc cat agc caa gaa cca aag gac cca cac gac ctc atg ttc acc att    816
Ile His Ser Gln Glu Pro Lys Asp Pro His Asp Leu Met Phe Thr Ile
                260                     265                     270 cac cgg agc aca ggc acc atc agc gtc atc tcc agt ggc ctg gac cgg    864
His Arg Ser Thr Gly Thr Ile Ser Val Ile Ser Ser Gly Leu Asp Arg
            275                     280                     285 gaa aaa gtc cct gag tac aca ctg acc atc cag gcc aca gac atg gat    912
Glu Lys Val Pro Glu Tyr Thr Leu Thr Ile Gln Ala Thr Asp Met Asp
        290                     295                     300 ggg gac ggc tcc acc acc acg gca gtg gca gta gtg gag atc ctt gat    960
Gly Asp Gly Ser Thr Thr Thr Ala Val Ala Val Val Glu Ile Leu Asp
305                     310                     315                 320 gcc aat gac aat gct ccc atg ttt gac ccc cag aag tac gag gcc cat    1008
Ala Asn Asp Asn Ala Pro Met Phe Asp Pro Gln Lys Tyr Glu Ala His
                    325                     330                     335 gtg cct gag aat gca gtg ggc cat gag gtg cag agg ctg acg gtc act    1056
Val Pro Glu Asn Ala Val Gly His Glu Val Gln Arg Leu Thr Val Thr
                340                     345                     350 gat ctg gac gcc ccc aac tca cca gcg tgg cgt gcc acc tac ctt atc    1104
Asp Leu Asp Ala Pro Asn Ser Pro Ala Trp Arg Ala Thr Tyr Leu Ile
            355                     360                     365 atg ggc ggt gac gac ggg gac cat ttt acc atc acc acc cac cct gag    1152
Met Gly Gly Asp Asp Gly Asp His Phe Thr Ile Thr Thr His Pro Glu
        370                     375                     380 agc aac cag ggc atc ctg aca acc agg aag ggt ttg gat ttt gag gcc    1200
Ser Asn Gln Gly Ile Leu Thr Thr Arg Lys Gly Leu Asp Phe Glu Ala
385                     390                     395                 400 aaa aac cag cac acc ctg tac gtt gaa gtg acc aac gag gcc cct ttt    1248
Lys Asn Gln His Thr Leu Tyr Val Glu Val Thr Asn Glu Ala Pro Phe
```

-continued

```
                    405                 410                 415
gtg ctg aag ctc cca acc tcc aca gcc acc ata gtg gtc cac gtg gag    1296
Val Leu Lys Leu Pro Thr Ser Thr Ala Thr Ile Val Val His Val Glu
            420                 425                 430 gat gtg aat gag gca cct gtg ttt gtc cca ccc tcc aaa gtc gtt gag    1344
Asp Val Asn Glu Ala Pro Val Phe Val Pro Pro Ser Lys Val Val Glu
            435                 440                 445 gtc cag gag ggc atc ccc act ggg gag cct gtg tgt gtc tac act gca    1392
Val Gln Glu Gly Ile Pro Thr Gly Glu Pro Val Cys Val Tyr Thr Ala
            450                 455                 460 gaa gac cct gac aag gag aat caa aag atc agc tac cgc atc ctg aga    1440
Glu Asp Pro Asp Lys Glu Asn Gln Lys Ile Ser Tyr Arg Ile Leu Arg
465                 470                 475                 480 gac cca gca ggg tgg cta gcc atg gac cca gac agt ggg cag gtc aca    1488
Asp Pro Ala Gly Trp Leu Ala Met Asp Pro Asp Ser Gly Gln Val Thr
            485                 490                 495 gct gtg ggc acc ctc gac cgt gag gat gag cag ttt gtg agg aac aac    1536
Ala Val Gly Thr Leu Asp Arg Glu Asp Glu Gln Phe Val Arg Asn Asn
            500                 505                 510 atc tat gaa gtc atg gtc ttg gcc atg gac aat gga agc cct ccc acc    1584
Ile Tyr Glu Val Met Val Leu Ala Met Asp Asn Gly Ser Pro Pro Thr
            515                 520                 525 act ggc acg gga acc ctt ctg cta aca ctg att gat gtc aat gac cat    1632
Thr Gly Thr Gly Thr Leu Leu Leu Thr Leu Ile Asp Val Asn Asp His
            530                 535                 540 ggc cca gtc cct gag ccc cgt cag atc acc atc tgc aac caa agc cct    1680
Gly Pro Val Pro Glu Pro Arg Gln Ile Thr Ile Cys Asn Gln Ser Pro
545                 550                 555                 560 gtg cgc cag gtg ctg aac atc acg gac aag gac ctg tct ccc cac acc    1728
Val Arg Gln Val Leu Asn Ile Thr Asp Lys Asp Leu Ser Pro His Thr
            565                 570                 575 tcc cct ttc cag gcc cag ctc aca gat gac tca gac atc tac tgg acg    1776
Ser Pro Phe Gln Ala Gln Leu Thr Asp Asp Ser Asp Ile Tyr Trp Thr
            580                 585                 590 gca gag gtc aac gag gaa ggt gac aca gtg gtc ttg tcc ctg aag aag    1824
Ala Glu Val Asn Glu Glu Gly Asp Thr Val Val Leu Ser Leu Lys Lys
            595                 600                 605 ttc ctg aag cag gat aca tat gac gtg cac ctt tct ctg tct gac cat    1872
Phe Leu Lys Gln Asp Thr Tyr Asp Val His Leu Ser Leu Ser Asp His
            610                 615                 620 ggc aac aaa gag cag ctg acg gtg atc agg gcc act gtg tgc gac tgc    1920
Gly Asn Lys Glu Gln Leu Thr Val Ile Arg Ala Thr Val Cys Asp Cys
625                 630                 635                 640 cat ggc cat gtc gaa acc tgc cct gga ccc tgg aag gga ggt ttc atc    1968
His Gly His Val Glu Thr Cys Pro Gly Pro Trp Lys Gly Gly Phe Ile
            645                 650                 655 ctc cct gtg ctg ggg gct gtc ctg gct ctg ctg ttc ctg ctg gtg        2016
Leu Pro Val Leu Gly Ala Val Leu Ala Leu Leu Phe Leu Leu Leu Val
            660                 665                 670 ctg ctt ttg ttg gtg aga aag aag cgg aag atc aag gag ccc ctc cta    2064
Leu Leu Leu Leu Val Arg Lys Lys Arg Lys Ile Lys Glu Pro Leu Leu
            675                 680                 685 ctc cca gaa gat gac acc cgt gac aac gtc ttc tac tat ggc gaa gag    2112
Leu Pro Glu Asp Asp Thr Arg Asp Asn Val Phe Tyr Tyr Gly Glu Glu
            690                 695                 700 ggg ggt ggc gaa gag gac cag gac tat gac atc acc cag ctc cac cga    2160
Gly Gly Gly Glu Glu Asp Gln Asp Tyr Asp Ile Thr Gln Leu His Arg
705                 710                 715                 720 ggt ctg gag gcc agg ccg gag gtg gtt ctc cgc aat gac gtg gca cca    2208
Gly Leu Glu Ala Arg Pro Glu Val Val Leu Arg Asn Asp Val Ala Pro
```

```
                   725                 730                 735
acc atc atc ccg aca ccc atg tac cgt cct cgg cca gcc aac cca gat     2256
Thr Ile Ile Pro Thr Pro Met Tyr Arg Pro Arg Pro Ala Asn Pro Asp
            740                 745                 750 gaa atc ggc aac ttt ata att gag aac ctg aag gcg gct aac aca gac     2304
Glu Ile Gly Asn Phe Ile Ile Glu Asn Leu Lys Ala Ala Asn Thr Asp
            755                 760                 765 ccc aca gcc ccg ccc tac gac acc ctc ttg gtg ttc gac tat gag ggc     2352
Pro Thr Ala Pro Pro Tyr Asp Thr Leu Leu Val Phe Asp Tyr Glu Gly
            770                 775                 780 agc ggc tcc gac gcc gcg tcc ctg agc tcc ctc acc tcc tcc gcc tcc     2400
Ser Gly Ser Asp Ala Ala Ser Leu Ser Ser Leu Thr Ser Ser Ala Ser
785                 790                 795                 800 gac caa gac caa gat tac gat tat ctg aac gag tgg ggc agc cgc ttc     2448
Asp Gln Asp Gln Asp Tyr Asp Tyr Leu Asn Glu Trp Gly Ser Arg Phe
                805                 810                 815 aag aag ctg gca gac atg tac ggt ggc ggg gag gac gac tag             2490
Lys Lys Leu Ala Asp Met Tyr Gly Gly Gly Glu Asp Asp
                820                 825
```

<210> SEQ ID NO 2
<211> LENGTH: 829
<212> TYPE: PRT
<213> ORGANISM: human

<400> SEQUENCE: 2

```
Met Gly Leu Pro Arg Gly Pro Leu Ala Ser Leu Leu Leu Leu Gln Val
1               5                   10                  15

Cys Trp Leu Gln Cys Ala Ala Ser Glu Pro Cys Arg Ala Val Phe Arg
            20                  25                  30

Glu Ala Glu Val Thr Leu Glu Ala Gly Gly Ala Glu Gln Glu Pro Gly
        35                  40                  45

Gln Ala Leu Gly Lys Val Phe Met Gly Cys Pro Gly Gln Glu Pro Ala
    50                  55                  60

Leu Phe Ser Thr Asp Asn Asp Asp Phe Thr Val Arg Asn Gly Glu Thr
65                  70                  75                  80

Val Gln Glu Arg Arg Ser Leu Lys Glu Arg Asn Pro Leu Lys Ile Phe
                85                  90                  95

Pro Ser Lys Arg Ile Leu Arg Arg His Lys Arg Asp Trp Val Val Ala
            100                 105                 110

Pro Ile Ser Val Pro Glu Asn Gly Lys Gly Pro Phe Pro Gln Arg Leu
        115                 120                 125

Asn Gln Leu Lys Ser Asn Lys Asp Arg Asp Thr Lys Ile Phe Tyr Ser
    130                 135                 140

Ile Thr Gly Pro Gly Ala Asp Ser Pro Pro Glu Gly Val Phe Ala Val
145                 150                 155                 160

Glu Lys Glu Thr Gly Trp Leu Leu Leu Asn Lys Pro Leu Asp Arg Glu
                165                 170                 175

Glu Ile Ala Lys Tyr Glu Leu Phe Gly His Ala Val Ser Glu Asn Gly
            180                 185                 190

Ala Ser Val Glu Asp Pro Met Asn Ile Ser Ile Ile Val Thr Asp Gln
        195                 200                 205

Asn Asp His Lys Pro Lys Phe Thr Gln Asp Thr Phe Arg Gly Ser Val
    210                 215                 220

Leu Glu Gly Val Leu Pro Gly Thr Ser Val Met Gln Val Thr Ala Thr
225                 230                 235                 240

Asp Glu Asp Asp Ala Ile Tyr Thr Tyr Asn Gly Val Val Ala Tyr Ser
```

```
                    245                 250                 255
Ile His Ser Gln Glu Pro Lys Asp Pro His Asp Leu Met Phe Thr Ile
            260                 265                 270

His Arg Ser Thr Gly Thr Ile Ser Val Ile Ser Ser Gly Leu Asp Arg
            275                 280                 285

Glu Lys Val Pro Glu Tyr Thr Leu Thr Ile Gln Ala Thr Asp Met Asp
            290                 295                 300

Gly Asp Gly Ser Thr Thr Thr Ala Val Ala Val Val Glu Ile Leu Asp
305                 310                 315                 320

Ala Asn Asp Asn Ala Pro Met Phe Asp Pro Gln Lys Tyr Glu Ala His
                    325                 330                 335

Val Pro Glu Asn Ala Val Gly His Glu Val Gln Arg Leu Thr Val Thr
                    340                 345                 350

Asp Leu Asp Ala Pro Asn Ser Pro Ala Trp Arg Ala Thr Tyr Leu Ile
            355                 360                 365

Met Gly Gly Asp Asp Gly Asp His Phe Thr Ile Thr Thr His Pro Glu
            370                 375                 380

Ser Asn Gln Gly Ile Leu Thr Thr Arg Lys Gly Leu Asp Phe Glu Ala
385                 390                 395                 400

Lys Asn Gln His Thr Leu Tyr Val Glu Val Thr Asn Glu Ala Pro Phe
                    405                 410                 415

Val Leu Lys Leu Pro Thr Ser Thr Ala Thr Ile Val Val His Val Glu
            420                 425                 430

Asp Val Asn Glu Ala Pro Val Phe Val Pro Ser Lys Val Val Glu
            435                 440                 445

Val Gln Glu Gly Ile Pro Thr Gly Glu Pro Val Cys Val Tyr Thr Ala
            450                 455                 460

Glu Asp Pro Asp Lys Glu Asn Gln Lys Ile Ser Tyr Arg Ile Leu Arg
465                 470                 475                 480

Asp Pro Ala Gly Trp Leu Ala Met Asp Pro Asp Ser Gly Gln Val Thr
            485                 490                 495

Ala Val Gly Thr Leu Asp Arg Glu Asp Glu Gln Phe Val Arg Asn Asn
            500                 505                 510

Ile Tyr Glu Val Met Val Leu Ala Met Asp Asn Gly Ser Pro Pro Thr
            515                 520                 525

Thr Gly Thr Gly Thr Leu Leu Leu Thr Leu Ile Asp Val Asn Asp His
            530                 535                 540

Gly Pro Val Pro Glu Pro Arg Gln Ile Thr Ile Cys Asn Gln Ser Pro
545                 550                 555                 560

Val Arg Gln Val Leu Asn Ile Thr Asp Lys Asp Leu Ser Pro His Thr
                    565                 570                 575

Ser Pro Phe Gln Ala Gln Leu Thr Asp Asp Ser Asp Ile Tyr Trp Thr
            580                 585                 590

Ala Glu Val Asn Glu Glu Gly Asp Thr Val Leu Ser Leu Lys Lys
            595                 600                 605

Phe Leu Lys Gln Asp Thr Tyr Asp Val His Leu Ser Leu Ser Asp His
            610                 615                 620

Gly Asn Lys Glu Gln Leu Thr Val Ile Arg Ala Thr Val Cys Asp Cys
625                 630                 635                 640

His Gly His Val Glu Thr Cys Pro Gly Pro Trp Lys Gly Phe Ile
                    645                 650                 655

Leu Pro Val Leu Gly Ala Val Leu Ala Leu Phe Leu Leu Leu Val
            660                 665                 670
```

```
Leu Leu Leu Leu Val Arg Lys Lys Arg Lys Ile Lys Glu Pro Leu Leu
            675                 680                 685

Leu Pro Glu Asp Asp Thr Arg Asp Asn Val Phe Tyr Tyr Gly Glu Glu
        690                 695                 700

Gly Gly Gly Glu Glu Asp Gln Asp Tyr Asp Ile Thr Gln Leu His Arg
705                 710                 715                 720

Gly Leu Glu Ala Arg Pro Glu Val Val Leu Arg Asn Asp Val Ala Pro
                725                 730                 735

Thr Ile Ile Pro Thr Pro Met Tyr Arg Pro Arg Pro Ala Asn Pro Asp
            740                 745                 750

Glu Ile Gly Asn Phe Ile Ile Glu Asn Leu Lys Ala Ala Asn Thr Asp
        755                 760                 765

Pro Thr Ala Pro Pro Tyr Asp Thr Leu Leu Val Phe Asp Tyr Glu Gly
    770                 775                 780

Ser Gly Ser Asp Ala Ala Ser Leu Ser Ser Leu Thr Ser Ser Ala Ser
785                 790                 795                 800

Asp Gln Asp Gln Asp Tyr Asp Tyr Leu Asn Glu Trp Gly Ser Arg Phe
                805                 810                 815

Lys Lys Leu Ala Asp Met Tyr Gly Gly Gly Glu Asp Asp
            820                 825

<210> SEQ ID NO 3
<211> LENGTH: 2040
<212> TYPE: DNA
<213> ORGANISM: human

<400> SEQUENCE: 3
agtggcgtcg gaactgcaaa gcacctgtga gcttgcggaa gtcagttcag actccagccc        60
gctccagccc ggcccgaccc gaccgcaccc ggcgcctgcc ctcgctcggc gtccccggcc       120
agccatgggc ccttggagcc gcagcctctc ggcgctgctg ctgctgctgc aggtctcctc       180
ttggctctgc caggagccgg agccctgcca ccctggcttt gacgccgaga gctacacgtt       240
cacggtgccc cggcgccacc tggagagagg ccgcgtcctg ggcagagtga attttgaaga       300
ttgcaccggt cgacaaagga cagcctattt tccctcgac acccgattca agtgggcac        360 agatggtgtg attacagtca aaaggcctct acggtttcat aacccacaga tccatttctt       420
ggtctacgcc tgggactcca cctacagaaa gttttccacc aaagtcacgc tgaatacagt       480
ggggcaccac caccgccccc cgccccatca ggcctccgtt tctggaatcc aagcagaatt       540
gctcacattt cccaactcct ctcctggcct cagaagacag aagagagact gggttattcc       600
tcccatcagc tgcccagaaa atgaaaaagg cccatttcct aaaaacctgg ttcagatcaa       660
atccaacaaa gacaaagaag gcaaggtttt ctacagcatc actggccaag agctgacac        720 accccctgtt ggtgtctttt tattgaaag agaaacagga tggctgaagg tgacagagcc       780
tctggataga gaacgcattg ccacatacac tctcttctct cacgctgtgt catccaacgg       840
gaatgcagtt gaggatccaa tggagatttt gatcacggta accgatcaga atgacaacaa       900
gcccgaattc acccaggagg tctttaaggg gtctgtcatg gaaggtgctc ttccaggaac       960
ctctgtgatg gaggtcacag ccacagacgc ggacgatgat gtgaacacct acaatgccgc      1020
catcgcttac accatcctca gccaagatcc tgagctccct gacaaaaata tgttcaccat      1080 taacagggaac acaggagtca tcagtgtggt caccactggg ctggaccgag agagtttccc      1140
tacgtatacc ctggtgggtc aagctgctga ccttcaaggt gaggggttaa gcacaacagc      1200
aacagctgtg atcacagtca ctgacaccaa cgataatcct ccgatcttca atcccaccac      1260
```

```
gtacaagggt caggtgcctg agaacgaggc taacgtcgta atcaccacac tgaaagtgac    1320
tgatgctgat gccccccaata ccccagcgtg ggaggctgta tacaccatat tgaatgatga    1380
tggtggacaa tttgtcgtca ccacaaatcc agtgaacaac gatggcattt tgaaaacagc    1440
aaagggcttg gattttgagg ccaagcagca gtacattcta cacgtagcag tgacgaatgt    1500 ggtaccttt gaggtctctc tcaccacctc cacagccacc gtcaccgtgg atgtgctgga    1560
tgtgaatgaa gccccatct ttgtgcctcc tgaaaagaga gtggaagtgt ccgaggactt    1620
tggcgtgggc caggaaatca catcctacac tgcccaggag ccagacacat ttatggaaca    1680
gaaaataaca tatcggattt ggagagacac tgccaactgg ctggagatta atccggacac    1740
tggtgccatt tccactcggg ctgagctgga cagggaggat tttgagcacg tgaagaacag    1800
cacgtacaca gccctaatca tagctacaga caatggttct ccagttgcta ctggaacagg    1860
gacacttctg ctgatcctgt ctgatgtgaa tgacaacgcc cccataccag aacctcgaac    1920
tatattcttc tgtgagagga atccaaagcc tcaggtcata aacatcattg atgcagacct    1980
tcctcccaat acatctccct tcacagcaga actaacacac ggggcgagtg ccaactggac    2040
```

<210> SEQ ID NO 4
<211> LENGTH: 882
<212> TYPE: PRT
<213> ORGANISM: human

<400> SEQUENCE: 4

Met Gly Pro Trp Ser Arg Ser Leu Ser Ala Leu Leu Leu Leu Leu Gln
1               5                   10                  15

Val Ser Ser Trp Leu Cys Gln Glu Pro Glu Pro Cys His Pro Gly Phe
            20                  25                  30

Asp Ala Glu Ser Tyr Thr Phe Thr Val Pro Arg Arg His Leu Glu Arg
        35                  40                  45

Gly Arg Val Leu Gly Arg Val Asn Phe Glu Asp Cys Thr Gly Arg Gln
    50                  55                  60

Arg Thr Ala Tyr Phe Ser Leu Asp Thr Arg Phe Lys Val Gly Thr Asp
65                  70                  75                  80

Gly Val Ile Thr Val Lys Arg Pro Leu Arg Phe His Asn Pro Gln Ile
                85                  90                  95

His Phe Leu Val Tyr Ala Trp Asp Ser Thr Tyr Arg Lys Phe Ser Thr
            100                 105                 110

Lys Val Thr Leu Asn Thr Val Gly His His Arg Pro Pro His
        115                 120                 125

Gln Ala Ser Val Ser Gly Ile Gln Ala Glu Leu Leu Thr Phe Pro Asn
    130                 135                 140

Ser Ser Pro Gly Leu Arg Arg Gln Lys Arg Asp Trp Val Ile Pro Pro
145                 150                 155                 160

Ile Ser Cys Pro Glu Asn Glu Lys Gly Pro Phe Pro Lys Asn Leu Val
                165                 170                 175

Gln Ile Lys Ser Asn Lys Asp Lys Glu Gly Lys Val Phe Tyr Ser Ile
            180                 185                 190

Thr Gly Gln Gly Ala Asp Thr Pro Pro Val Gly Val Phe Ile Ile Glu
        195                 200                 205

Arg Glu Thr Gly Trp Leu Lys Val Thr Glu Pro Leu Asp Arg Glu Arg
    210                 215                 220

Ile Ala Thr Tyr Thr Leu Phe Ser His Ala Val Ser Ser Asn Gly Asn
225                 230                 235                 240

Ala Val Glu Asp Pro Met Glu Ile Leu Ile Thr Val Thr Asp Gln Asn

```
                245                 250                 255
Asp Asn Lys Pro Glu Phe Thr Gln Glu Val Phe Lys Gly Ser Val Met
            260                 265                 270

Glu Gly Ala Leu Pro Gly Thr Ser Val Met Glu Val Thr Ala Thr Asp
            275                 280                 285

Ala Asp Asp Val Asn Thr Tyr Asn Ala Ala Ile Ala Tyr Thr Ile
            290                 295                 300

Leu Ser Gln Asp Pro Glu Leu Pro Asp Lys Asn Met Phe Thr Ile Asn
305                 310                 315                 320

Arg Asn Thr Gly Val Ile Ser Val Val Thr Thr Gly Leu Asp Arg Glu
                325                 330                 335

Ser Phe Pro Thr Tyr Thr Leu Val Val Gln Ala Ala Asp Leu Gln Gly
            340                 345                 350

Glu Gly Leu Ser Thr Thr Ala Thr Ala Val Ile Thr Val Thr Asp Thr
            355                 360                 365

Asn Asp Asn Pro Pro Ile Phe Asn Pro Thr Thr Tyr Lys Gly Gln Val
            370                 375                 380

Pro Glu Asn Glu Ala Asn Val Val Ile Thr Thr Leu Lys Val Thr Asp
385                 390                 395                 400

Ala Asp Ala Pro Asn Thr Pro Ala Trp Glu Ala Val Tyr Thr Ile Leu
                405                 410                 415

Asn Asp Asp Gly Gly Gln Phe Val Val Thr Thr Asn Pro Val Asn Asn
                420                 425                 430

Asp Gly Ile Leu Lys Thr Ala Lys Gly Leu Asp Phe Glu Ala Lys Gln
            435                 440                 445

Gln Tyr Ile Leu His Val Ala Val Thr Asn Val Val Pro Phe Glu Val
            450                 455                 460

Ser Leu Thr Thr Ser Thr Ala Thr Val Thr Val Asp Val Leu Asp Val
465                 470                 475                 480

Asn Glu Ala Pro Ile Phe Val Pro Pro Glu Lys Arg Val Glu Val Ser
                485                 490                 495

Glu Asp Phe Gly Val Gly Gln Glu Ile Thr Ser Tyr Thr Ala Gln Glu
            500                 505                 510

Pro Asp Thr Phe Met Glu Gln Lys Ile Thr Tyr Arg Ile Trp Arg Asp
            515                 520                 525

Thr Ala Asn Trp Leu Glu Ile Asn Pro Asp Thr Gly Ala Ile Ser Thr
            530                 535                 540

Arg Ala Glu Leu Asp Arg Glu Asp Phe Glu His Val Lys Asn Ser Thr
545                 550                 555                 560

Tyr Thr Ala Leu Ile Ile Ala Thr Asp Asn Gly Ser Pro Val Ala Thr
                565                 570                 575

Gly Thr Gly Thr Leu Leu Leu Ile Leu Ser Asp Val Asn Asp Asn Ala
            580                 585                 590

Pro Ile Pro Glu Pro Arg Thr Ile Phe Phe Cys Glu Arg Asn Pro Lys
            595                 600                 605

Pro Gln Val Ile Asn Ile Ile Asp Ala Asp Leu Pro Pro Asn Thr Ser
            610                 615                 620

Pro Phe Thr Ala Glu Leu Thr His Gly Ala Ser Ala Asn Trp Thr Ile
625                 630                 635                 640

Gln Tyr Asn Asp Pro Thr Gln Glu Ser Ile Ile Leu Lys Pro Lys Met
                645                 650                 655

Ala Leu Glu Val Gly Asp Tyr Lys Ile Asn Leu Lys Leu Met Asp Asn
            660                 665                 670
```

```
Gln Asn Lys Asp Gln Val Thr Thr Leu Glu Val Ser Val Cys Asp Cys
    675                 680                 685
Glu Gly Ala Ala Gly Val Cys Arg Lys Ala Gln Pro Val Glu Ala Gly
690                 695                 700
Leu Gln Ile Pro Ala Ile Leu Gly Ile Leu Gly Gly Ile Leu Ala Leu
705                 710                 715                 720
Leu Ile Leu Ile Leu Leu Leu Leu Phe Leu Arg Arg Arg Ala Val
            725                 730                 735
Val Lys Glu Pro Leu Leu Pro Pro Glu Asp Asp Thr Arg Asp Asn Val
            740                 745                 750
Tyr Tyr Tyr Asp Glu Glu Gly Gly Glu Glu Asp Gln Asp Phe Asp
            755                 760                 765
Leu Ser Gln Leu His Arg Gly Leu Asp Ala Arg Pro Glu Val Thr Arg
770                 775                 780
Asn Asp Val Ala Pro Thr Leu Met Ser Val Pro Arg Tyr Leu Pro Arg
785                 790                 795                 800
Pro Ala Asn Pro Asp Glu Ile Gly Asn Phe Ile Asp Glu Asn Leu Lys
            805                 810                 815
Ala Ala Asp Thr Asp Pro Thr Ala Pro Pro Tyr Asp Ser Leu Leu Val
            820                 825                 830
Phe Asp Tyr Glu Gly Ser Gly Ser Glu Ala Ala Ser Leu Ser Ser Leu
            835                 840                 845
Asn Ser Ser Glu Ser Asp Lys Asp Gln Asp Tyr Asp Tyr Leu Asn Glu
850                 855                 860
Trp Gly Asn Arg Phe Lys Lys Leu Ala Asp Met Tyr Gly Gly Gly Glu
865                 870                 875                 880
Asp Asp

<210> SEQ ID NO 5
<211> LENGTH: 4380
<212> TYPE: DNA
<213> ORGANISM: human

<400> SEQUENCE: 5
ggggagcgcc atccgctcca cttccacctc cacatcctcc accggccaag gtccccgccg      60
ctgcatccct cgcggcttcc gctgcgctcc gggccggagc cgagccgcct cgcgctgccac   120
agcagccgcc tccacacact cgcagacgct cacacgctct ccctccctgt tccccgccc    180
cctccccagc tccttgatct ctgggtctgt tttattactc ctggtgcgag tcccgcggac   240
tccgcggccc gctatttgtc atcagctcgc tctccattgg cggggagcgg agagcagcga   300
agaaggggt ggggagggga ggggaaggga aggggtgga aactgcctgg agccgttct     360
ccgcgccgct gttggtgctg ccgctgcctc ctcctcctcc gccgccgccg ccgccgccgc   420
cgcctcctcc ggctcttcgc tcggcccctc tccgcctcca tgtgccggat agcgggagcg   480
ctgcggaccc tgctgccgct gctggcggcc ctgcttcagg cgtctgtaga ggcttctggt   540
gaaatcgcat tatgcaagac tggatttcct gaagatgttt acagtgcagt cttatcgaag   600
gatgtgcatg aaggacagcc tcttctcaat gtgaagtta gcaactgcaa tggaaaaga    660
aaagtacaat atgagagcag tgagcctgca gattttaagg tggatgaaga tggcatggtg   720
tatgccgtga aagctttcc actctcttct gagcatgcca agttcctgat atatgcccaa   780
gacaaagaga cccaggaaaa gtggcaagtg gcagtaaaat tgagcctgaa gccaaccta   840
actgaggagt cagtgaagga gtcagcagaa gttgaagaaa tagtgttccc aagacaattc   900
agtaagcaca gtggccacct acaaaggcag aagagagact gggtcatccc tccaatcaac   960
```

```
ttgccagaaa actccagggg accttttcct caagagcttg tcaggatcag gtctgataga    1020
gataaaaacc tttcactgcg gtacagtgta actgggccag gagctgacca gcctccaact    1080
ggtatcttca ttatcaaccc catctcgggt cagctgtcgg tgacaaagcc cctggatcgc    1140
gagcagatag cccggtttca tttgagggca catgcagtag atattaatgg aaatcaagtg    1200
gagaacccca ttgacattgt catcaatgtt attgacatga atgacaacag acctgagttc    1260
ttacaccagg tttggaatgg gacagttcct gagggatcaa agcctggaac atatgtgatg    1320
accgtaacag caattgatgc tgacgatccc aatgccctca atgggatgtt gaggtacaga    1380
atcgtgtctc aggctccaag cacccctttca cccaacatgt ttacaatcaa caatgagact    1440
ggtgacatca tcacagtggc agctggactt gatcgagaaa aagtgcaaca gtatacgtta    1500
ataattcaag ctacagacat ggaaggcaat cccacatatg gcctttcaaa cacagccacg    1560
gccgtcatca cagtgacaga tgtcaatgac aatcctccag agtttactgc catgacgttt    1620
tatggtgaag ttcctgagaa cagggtagac atcatagtag ctaatctaac tgtgaccgat    1680
aaggatcaac cccatacacc agcctggaac gcagtgtaca gaatcagtgg cggagatcct    1740 actgacggt tcgccatcca gaccgaccca acagcaacg acgggttagt caccgtggtc    1800
aaaccaatcg actttgaaac aaataggatg tttgtcctta ctgttgctgc agaaaatcaa    1860
gtgccattag ccaagggaat tcagcacccg cctcagtcaa ctgcaaccgt gtctgttaca    1920
gttattgacg taaatgaaaa cccttatttt gcccccaatc ctaagatcat tcgccaagaa    1980
gaagggcttc atgccggtac catgttgaca acattcactg ctcaggaccc agatcgatat    2040
atgcagcaaa atattagata cactaaatta tctgatcctg ccaattggct aaaaatagat    2100
cctgtgaatg gacaaataac tacaattgct gttttggacc gagaatcacc aaatgtgaaa    2160
aacaatatat ataatgctac tttccttgct tctgacaatg gaattcctcc tatgagtgga    2220
acaggaacgc tgcagatcta tttacttgat attaatgaca tgcccctca gtgttacct    2280 caagaggcag agacttgcga aactccagac cccaattcaa ttaatattac agcacttgat    2340
tatgacattg atccaaatgc tggaccattt gcttttgatc ttcctttatc tccagtgact    2400
attaagagaa attggaccat cactcggctt aatggtgatt ttgctcagct taatttaaag    2460
ataaaatttc ttgaagctgg tatctatgaa gttcccatca taatcacaga ttcgggtaat    2520
cctcccaaat caaatatttc catcctgcgc gtgaaggttt gccagtgtga ctccaacggg    2580
gactgcacag atgtggacag gattgtgggt gcggggcttg gcaccggtgc catcattgcc    2640
atcctgctct gcatcatcat cctgcttatc cttgtgctga tgtttgtggt atggatgaaa    2700
cgccgggata agaacgcca ggccaaacaa cttttaattg atccagaaga tgatgtaaga    2760
gataatattt taaaatatga tgaagaaggt ggaggagaag aagaccagga ctatgacttg    2820
agccagctgc agcagcctga cactgtggag cctgatgcca tcaagcctgt gggaatccga    2880
cgaatggatg aaagacccat ccacgccgag ccccagtatc cggtccgatc tgcagcccca    2940
caccctggag acattgggga cttcattaat gagggcctta agcggctga caatgacccc    3000 acagctccac catatgactc cctgttagtg tttgactatg aaggcagtgg ctccactgct    3060
gggtccttga gctcccttaa ttcctcaagt agtggtggtg agcaggacta tgattacctg    3120
aacgactggg ggcacggtt caagaaactt gctgacatgt atggtggagg tgatgactga    3180
acttcagggt gaacttggtt tttggacaag tacaaacaat ttcaactgat attcccaaaa    3240
agcattcaga agctaggctt taactttgta gtctactagc acagtgcttg ctggaggctt    3300
tggcataggc tgcaaaccaa tttgggctca gagggaatat cagtgatcca tactgtttgg    3360
```

```
aaaaacactg agctcagtta cacttgaatt ttacagtaca gaagcactgg gattttatgt    3420 gccttttgt  accttttca  gattggaatt agttttctgt ttaaggcttt aatggtactg    3480
atttctgaaa cgataagtaa aagacaaaat attttgtggt gggagcagta agttaaacca    3540
tgatatgctt caacacgctt ttgttacatt gcatttgctt ttattaaaat acaaaattaa    3600
acaaacaaaa aaactcatgg agcgatttta ttatcttggg ggatgagacc atgagattgg    3660
aaaatgtaca ttacttctag ttttagactt tagtttgttt ttttttttt  cactaaaatc    3720 ttaaaactta ctcagctggt tgcaaataaa gggagttttc atatcaccaa tttgtagcaa    3780
aattgaattt tttcataaac tagaatgtta gacacatttt ggtcttaatc catgtacact    3840
tttttatttc tgtatttttc cacttcactg taaaaatagt atgtgtacat aatgttttat    3900
tggcatagtc tatggagaag tgcagaaact tcagaacatg tgtatgtatt atttggacta    3960
tggattcagg ttttttgcat gtttatatct ttcgttatgg ataaagtatt tacaaaacag    4020
tgacatttga ttcaattgtt gagctgtagt tagaatactc aattttttaat tttttttaatt   4080 tttttatttt ttattttctt tttggtttgg ggagggagaa aagttcttag cacaaatgtt    4140
ttacataatt tgtaccaaaa aaaaaaaaaa aggaaaggaa agaaaggggt ggcctgacac    4200
tggtggcact actaagtgtg tgttttttta aaaaaaaaat ggaaaaaaaa aagcttttaa    4260
actggagaga cttctgacaa cagctttgcc tctgtattgt gtaccagaat ataaatgata    4320
cacctctgac cccagcgttc tgaataaaat gctaattttg gatctggaaa aaaaaaaaa     4380

<210> SEQ ID NO 6
<211> LENGTH: 906
<212> TYPE: PRT
<213> ORGANISM: human

<400> SEQUENCE: 6

Met Cys Arg Ile Ala Gly Ala Leu Arg Thr Leu Leu Pro Leu Leu Ala
1               5                   10                  15

Ala Leu Leu Gln Ala Ser Val Glu Ala Ser Gly Glu Ile Ala Leu Cys
                20                  25                  30

Lys Thr Gly Phe Pro Glu Asp Val Tyr Ser Ala Val Leu Ser Lys Asp
            35                  40                  45

Val His Glu Gly Gln Pro Leu Leu Asn Val Lys Phe Ser Asn Cys Asn
        50                  55                  60

Gly Lys Arg Lys Val Gln Tyr Glu Ser Ser Glu Pro Ala Asp Phe Lys
65                  70                  75                  80

Val Asp Glu Asp Gly Met Val Tyr Ala Val Arg Ser Phe Pro Leu Ser
                85                  90                  95

Ser Glu His Ala Lys Phe Leu Ile Tyr Ala Gln Asp Lys Glu Thr Gln
            100                 105                 110

Glu Lys Trp Gln Val Ala Val Lys Leu Ser Leu Lys Pro Thr Leu Thr
        115                 120                 125

Glu Glu Ser Val Lys Glu Ser Ala Glu Val Glu Glu Ile Val Phe Pro
    130                 135                 140

Arg Gln Phe Ser Lys His Ser Gly His Leu Gln Arg Gln Lys Arg Asp
145                 150                 155                 160

Trp Val Ile Pro Pro Ile Asn Leu Pro Glu Asn Ser Arg Gly Pro Phe
                165                 170                 175

Pro Gln Glu Leu Val Arg Ile Arg Ser Asp Arg Asp Lys Asn Leu Ser
            180                 185                 190

Leu Arg Tyr Ser Val Thr Gly Pro Gly Ala Asp Gln Pro Pro Thr Gly
```

```
            195                 200                 205
Ile Phe Ile Ile Asn Pro Ile Ser Gly Gln Leu Ser Val Thr Lys Pro
210                 215                 220

Leu Asp Arg Glu Gln Ile Ala Arg Phe His Leu Arg Ala His Ala Val
225                 230                 235                 240

Asp Ile Asn Gly Asn Gln Val Glu Asn Pro Ile Asp Ile Val Ile Asn
                    245                 250                 255

Val Ile Asp Met Asn Asp Asn Arg Pro Glu Phe Leu His Gln Val Trp
                260                 265                 270

Asn Gly Thr Val Pro Glu Gly Ser Lys Pro Gly Thr Tyr Val Met Thr
                275                 280                 285

Val Thr Ala Ile Asp Ala Asp Pro Asn Ala Leu Asn Gly Met Leu
                290                 295                 300

Arg Tyr Arg Ile Val Ser Gln Ala Pro Ser Thr Pro Ser Pro Asn Met
305                 310                 315                 320

Phe Thr Ile Asn Asn Glu Thr Gly Asp Ile Ile Thr Val Ala Ala Gly
                    325                 330                 335

Leu Asp Arg Glu Lys Val Gln Gln Tyr Thr Leu Ile Ile Gln Ala Thr
                340                 345                 350

Asp Met Glu Gly Asn Pro Thr Tyr Gly Leu Ser Asn Thr Ala Thr Ala
                355                 360                 365

Val Ile Thr Val Thr Asp Val Asn Asp Asn Pro Glu Phe Thr Ala
                370                 375                 380

Met Thr Phe Tyr Gly Glu Val Pro Glu Asn Arg Val Asp Ile Ile Val
385                 390                 395                 400

Ala Asn Leu Thr Val Thr Asp Lys Asp Gln Pro His Thr Pro Ala Trp
                    405                 410                 415

Asn Ala Val Tyr Arg Ile Ser Gly Gly Asp Pro Thr Gly Arg Phe Ala
                420                 425                 430

Ile Gln Thr Asp Pro Asn Ser Asn Asp Gly Leu Val Thr Val Val Lys
                435                 440                 445

Pro Ile Asp Phe Glu Thr Asn Arg Met Phe Val Leu Thr Val Ala Ala
450                 455                 460

Glu Asn Gln Val Pro Leu Ala Lys Gly Ile Gln His Pro Pro Gln Ser
465                 470                 475                 480

Thr Ala Thr Val Ser Val Thr Val Ile Asp Val Asn Glu Asn Pro Tyr
                    485                 490                 495

Phe Ala Pro Asn Pro Lys Ile Ile Arg Gln Glu Glu Gly Leu His Ala
                500                 505                 510

Gly Thr Met Leu Thr Thr Phe Thr Ala Gln Asp Pro Asp Arg Tyr Met
                515                 520                 525

Gln Gln Asn Ile Arg Tyr Thr Lys Leu Ser Asp Pro Ala Asn Trp Leu
                530                 535                 540

Lys Ile Asp Pro Val Asn Gly Gln Ile Thr Thr Ile Ala Val Leu Asp
545                 550                 555                 560

Arg Glu Ser Pro Asn Val Lys Asn Asn Ile Tyr Asn Ala Thr Phe Leu
                    565                 570                 575

Ala Ser Asp Asn Gly Ile Pro Pro Met Ser Gly Thr Gly Thr Leu Gln
                580                 585                 590

Ile Tyr Leu Leu Asp Ile Asn Asp Asn Ala Pro Gln Val Leu Pro Gln
                595                 600                 605

Glu Ala Glu Thr Cys Glu Thr Pro Asp Pro Asn Ser Ile Asn Ile Thr
610                 615                 620
```

-continued

Ala Leu Asp Tyr Asp Ile Asp Pro Asn Ala Gly Pro Phe Ala Phe Asp
625                 630                 635                 640

Leu Pro Leu Ser Pro Val Thr Ile Lys Arg Asn Trp Thr Ile Thr Arg
            645                 650                 655

Leu Asn Gly Asp Phe Ala Gln Leu Asn Leu Lys Ile Lys Phe Leu Glu
            660                 665                 670

Ala Gly Ile Tyr Glu Val Pro Ile Ile Thr Asp Ser Gly Asn Pro
        675                 680                 685

Pro Lys Ser Asn Ile Ser Ile Leu Arg Val Lys Val Cys Gln Cys Asp
690                 695                 700

Ser Asn Gly Asp Cys Thr Asp Val Asp Arg Ile Val Gly Ala Gly Leu
705                 710                 715                 720

Gly Thr Gly Ala Ile Ile Ala Ile Leu Leu Cys Ile Ile Ile Leu Leu
                725                 730                 735

Ile Leu Val Leu Met Phe Val Val Trp Met Lys Arg Arg Asp Lys Glu
            740                 745                 750

Arg Gln Ala Lys Gln Leu Leu Ile Asp Pro Glu Asp Val Arg Asp
            755                 760                 765

Asn Ile Leu Lys Tyr Asp Glu Glu Gly Gly Glu Glu Asp Gln Asp
770                 775                 780

Tyr Asp Leu Ser Gln Leu Gln Gln Pro Asp Thr Val Glu Pro Asp Ala
785                 790                 795                 800

Ile Lys Pro Val Gly Ile Arg Arg Met Asp Glu Arg Pro Ile His Ala
                805                 810                 815

Glu Pro Gln Tyr Pro Val Arg Ser Ala Ala Pro His Pro Gly Asp Ile
            820                 825                 830

Gly Asp Phe Ile Asn Glu Gly Leu Lys Ala Ala Asp Asn Asp Pro Thr
            835                 840                 845

Ala Pro Pro Tyr Asp Ser Leu Leu Val Phe Asp Tyr Glu Gly Ser Gly
850                 855                 860

Ser Thr Ala Gly Ser Leu Ser Ser Leu Asn Ser Ser Ser Ser Gly Gly
865                 870                 875                 880

Glu Gln Asp Tyr Asp Tyr Leu Asn Asp Trp Gly Pro Arg Phe Lys Lys
            885                 890                 895

Leu Ala Asp Met Tyr Gly Gly Gly Asp Asp
            900                 905

<210> SEQ ID NO 7
<211> LENGTH: 24
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 7
cgcggtacca tggggctccc tcgt                                          24

<210> SEQ ID NO 8
<211> LENGTH: 29
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 8
ccgtctagat aacctccctt ccagggtcc                                     29

<210> SEQ ID NO 9
<211> LENGTH: 41
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 9
tatggagctc ggtaccgatt gggtggttgc tccaatatct g                    41

<210> SEQ ID NO 10
<211> LENGTH: 44
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 10
agattaccta tctagactac tgcatcacag aagtacctgg tagg                 44

<210> SEQ ID NO 11
<211> LENGTH: 43
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 11
tatggagctc ggtaccaagt ctaataaaga tagagacacc aag                  43

<210> SEQ ID NO 12
<211> LENGTH: 50
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 12
agattaccta tctagactac ctctgcacct catggcccac tgcattctca           50

<210> SEQ ID NO 13
<211> LENGTH: 41
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 13
tatggagctc ggtaccgtga cagccacgga tgaggatgat g                    41

<210> SEQ ID NO 14
<211> LENGTH: 41
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 14
agattaccta tctagactag acacacacag gctccccagt g                    41

<210> SEQ ID NO 15

```
<211> LENGTH: 38
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 15
tatggagctc ggtaccctga cggtcactga tctggacg                            38

<210> SEQ ID NO 16
<211> LENGTH: 47
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 16
agattaccta tctagactag ggctcaggga ctgggccatg gtcattg                  47

<210> SEQ ID NO 17
<211> LENGTH: 41
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 17
tatggagctc ggtacctaca ctgcagaaga ccctgacaag g                        41

<210> SEQ ID NO 18
<211> LENGTH: 50
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 18
agattaccta tctagactaa cctcccttcc agggtccagg gcaggtttcg               50
```